United States Patent
Walker

(10) Patent No.: US 11,478,156 B2
(45) Date of Patent: Oct. 25, 2022

(54) ATHLETIC PERFORMANCE MONITORING SYSTEM UTILIZING HEART RATE INFORMATION

(71) Applicant: NIKE, Inc., Beaverton, OR (US)

(72) Inventor: Steven H. Walker, Camas, WA (US)

(73) Assignee: NIKE, Inc., Beaverton, OR (US)

( * ) Notice: Subject to any disclaimer, the term of this patent is extended or adjusted under 35 U.S.C. 154(b) by 966 days.

(21) Appl. No.: 16/239,768

(22) Filed: Jan. 4, 2019

(65) Prior Publication Data

US 2019/0133458 A1 May 9, 2019

Related U.S. Application Data

(63) Continuation of application No. 14/063,767, filed on Oct. 25, 2013, now Pat. No. 10,206,589.

(Continued)

(51) Int. Cl.
*A61B 5/0205* (2006.01)
*A61B 5/024* (2006.01)
(Continued)

(52) U.S. Cl.
CPC ........ *A61B 5/0205* (2013.01); *A61B 5/02433* (2013.01); *A61B 5/11* (2013.01); *A61B 5/1128* (2013.01); *A61B 5/681* (2013.01); *A61B 5/002* (2013.01); *A61B 5/0022* (2013.01); *A61B 5/01* (2013.01); *A61B 5/02055* (2013.01);
(Continued)

(58) Field of Classification Search
CPC ..... A61B 5/0205; A61B 5/02433; A61B 5/11; A61B 5/1128; A61B 5/681; A61B 5/002; A61B 5/0022; A61B 5/01; A61B 5/02055; A61B 5/1112; A61B 5/4812;
(Continued)

(56) References Cited

U.S. PATENT DOCUMENTS

| 6,553,242 | B1 | 4/2003 | Sarussi | |
| 7,486,386 | B1* | 2/2009 | Holcombe | G01S 17/04 356/5.1 |
| 2002/0188210 | A1 | 12/2002 | Aizawa | |
| 2010/0305418 | A1* | 12/2010 | Deliwala | G01S 17/87 600/324 |
| 2011/0054809 | A1 | 3/2011 | Templeman | |

(Continued)

FOREIGN PATENT DOCUMENTS

| EP | 1520514 A1 | 4/2005 |
| JP | 2002000575 A | 1/2002 |

(Continued)

OTHER PUBLICATIONS

PCT International Search Report, PCT/US2013/066865, dated Jan. 22, 2014.

*Primary Examiner* — Sean P Dougherty
*Assistant Examiner* — Alexander H Connor
(74) *Attorney, Agent, or Firm* — Banner & Witcoff, Ltd.

(57) ABSTRACT

An illumination source may be configured to illuminate the skin of the user. An illumination detector may detect electromagnetic radiation reflected of the skin of the user. A compensation module may be configured to determine the position of the skin of the user relative to the illumination detector. A processor may be configured to determine a heart rate of the user by analyzing information corresponding to an amount of the electromagnetic radiation detected by the illumination detector. The processor may also determine the heart rate of the user by compensating for the position of the skin of the user as determined by the compensation module.

15 Claims, 9 Drawing Sheets

Related U.S. Application Data

(60) Provisional application No. 61/719,172, filed on Oct. 26, 2012.

(51) Int. Cl.
  *A61B 5/11* (2006.01)
  *A61B 5/00* (2006.01)
  *A61B 5/01* (2006.01)

(52) U.S. Cl.
  CPC ........... *A61B 5/1112* (2013.01); *A61B 5/4812* (2013.01); *A61B 5/6844* (2013.01); *A61B 5/721* (2013.01); *A61B 5/742* (2013.01); *A61B 5/7475* (2013.01)

(58) Field of Classification Search
  CPC ....... A61B 5/6844; A61B 5/721; A61B 5/742; A61B 5/7475; A61B 5/741
  See application file for complete search history.

(56) References Cited

U.S. PATENT DOCUMENTS

| | | |
|---|---|---|
| 2011/0092790 A1 | 4/2011 | Wilder-Smith et al. |
| 2012/0150052 A1 | 6/2012 | Buchheim et al. |

FOREIGN PATENT DOCUMENTS

| | | |
|---|---|---|
| JP | 2004261366 A | 9/2004 |
| JP | 2009213767 A | 9/2009 |
| JP | 2011050745 A | 3/2011 |
| JP | 2011206286 A | 10/2011 |
| KR | 20110014195 A | 2/2011 |
| KR | 20120098854 A | 9/2012 |
| KR | 20140024845 A | 3/2014 |
| WO | 90004941 A1 | 5/1990 |
| WO | 2005046476 A1 | 5/2005 |
| WO | 2010138385 A1 | 12/2010 |
| WO | 2012135325 A2 | 10/2012 |

\* cited by examiner

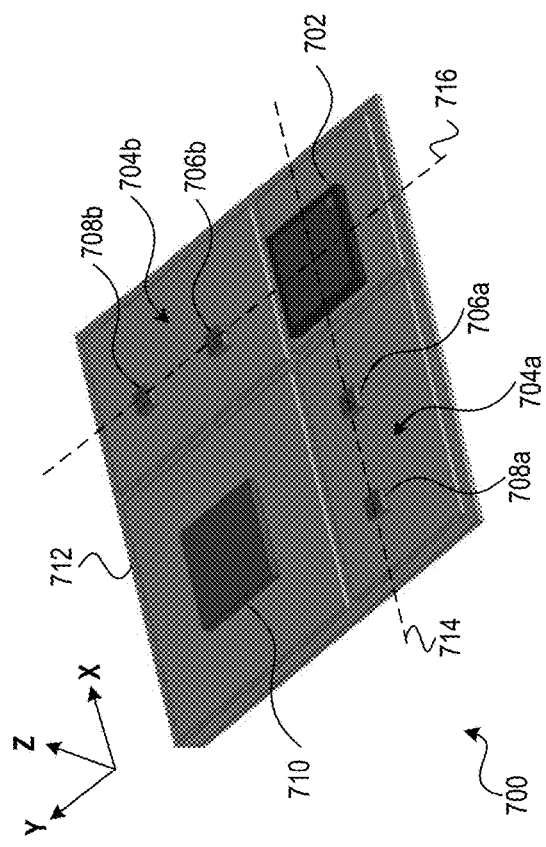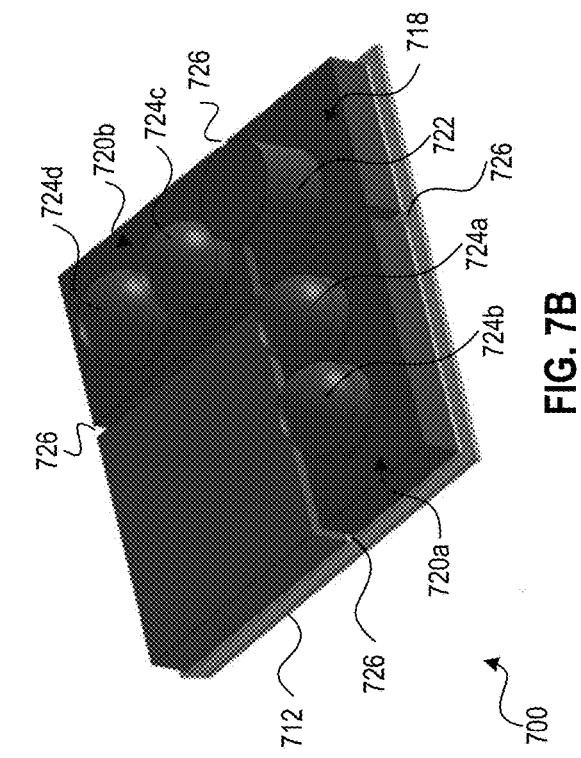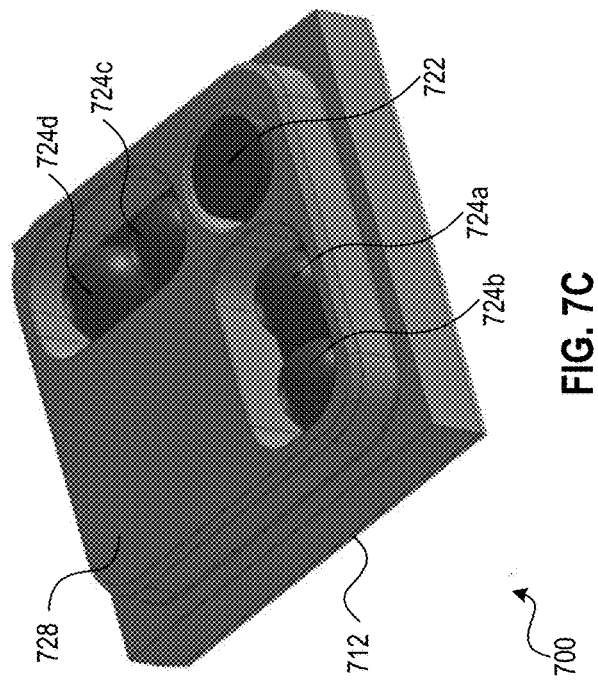
FIG. 7A
FIG. 7B
FIG. 7C

ATHLETIC PERFORMANCE MONITORING SYSTEM UTILIZING HEART RATE INFORMATION

CROSS-REFERENCE TO RELATED APPLICATION

This application is a continuation of U.S. patent application Ser. No. 14/063,767 entitled "Athletic Performance Monitoring System Utilizing Heart Rate Information" and filed on Oct. 25, 2013, which claims the benefit of U.S. Provisional Patent Application No. 61/719,172 entitled "Athletic Performance Monitoring System Utilizing Heart Rate Information" and filed on Oct. 26, 2012, which is incorporated by reference herein in its entirety.

TECHNICAL FIELD

The invention relates generally to athletic performance monitoring systems, and more particularly, to such systems that utilize heart rate information.

BACKGROUND

Accurate heart rate measurements may improve the utility of wrist-worn devices that measure the movements and activities of a user and provide activity points in response. For some work outs, the activity may involve substantially static movements that work mainly against gravity but are nonetheless strenuous. Examples include yoga, weight lifting, and other isometric exercises. Utilizing an accelerometer as the sole sensing element for these types of activities may result in an underestimating of the activity if the recorded movement is minimal compared to other activities that involve larger movements such as running or dancing in which the heart rate is strongly associated with the intensity of the movement. The addition of heart rate to the activity estimation algorithms greatly improves the range of activities in which an accurate estimate of activity occurs.

When measuring heart rate for sports-related activities and other types of activities, it is desirable that the heart rate sensor is portable and non-invasive. Existing technologies that may be used to measure heart rate, such as electrocardiography (ECG), may not be suited for some types of activities. Although some existing technologies to measure heart rate have been incorporated into devices that may be worn by a user, these existing technologies may require a user to actively select a button at the device to initiate the heart rate measurement. Moreover, existing device that may be worn by a user may require the device to be in intimate contact with the skin of the user in order to perform an accurate heart rate measurement. Such requirements may not be feasible in order to measure the heart rate of a user contemporaneous with performance of an activity by the user. In addition, existing devices that may be worn by users, such as a chest strap may be uncomfortable.

A full discussion of the features and advantages of the present invention is deferred to the following detailed description, which proceeds with reference to the accompanying drawings.

SUMMARY

The following presents a general summary of aspects of the invention in order to provide a basic understanding of at least some of its aspects. This summary is not an extensive overview of the invention. It is not intended to identify key or critical elements of the invention or to delineate the scope of the invention. The following summary merely presents some concepts of the invention in a general form as a prelude to the more detailed description provided below.

A first aspect described herein provides a method of determining heart rate. The skin of a user may be illuminated with an illumination source. An illumination detector may detect electromagnetic radiation reflected off the skin of the user. The position of the skin relative to the illumination detector may be determined based on the electromagnetic radiation reflected. A processor may determine a heart rate of the user by analyzing information corresponding to the electromagnetic radiation reflected and compensating for the position of the skin of the user.

A second aspect described herein provides a heart rate determination system. An illumination source may be configured to illuminate the skin of the user. An illumination detector may detect electromagnetic radiation reflected of the skin of the user. A compensation module may be configured to determine the position of the skin of the user relative to the illumination detector. A processor may be configured to determine a heart rate of the user by analyzing information corresponding to an amount of the electromagnetic radiation detected by the illumination detector. The processor may also determine the heart rate of the user by compensating for the position of the skin of the user as determined by the compensation module.

A third aspect described herein provides an optical detector. The optical detector may include two illumination modules positioned orthogonally relative to one another. Each illumination module may include a near-field LED and a far-field LED. The LEDs may be configured to provide infrared illumination. An illumination detector may include a photodiode that is configured to detect an amount of IR radiation reflected of the skin of a user. The photodiode may be offset from at least one of the centerlines of the optical detection module. An interface may be configured to provide information corresponding to the amount of IR illumination reflected off the skin of the user.

These aspects and additional aspects will be appreciated with the benefit of the detailed described provided below.

BRIEF DESCRIPTION OF THE DRAWINGS

Some example implementations are illustrated by way of example, and not by way of limitation, in the figures of the accompanying drawings and in which like reference numerals refer to similar elements.

FIG. 7A is a perspective view of another example of an implementation of a detection module of a heart rate monitor.

FIG. 7B is another perspective view of the detection module of FIG. 7A.

FIG. 7C is an additional perspective view of the detection module of FIG. 7A.

DETAILED DESCRIPTION

Figure 2:
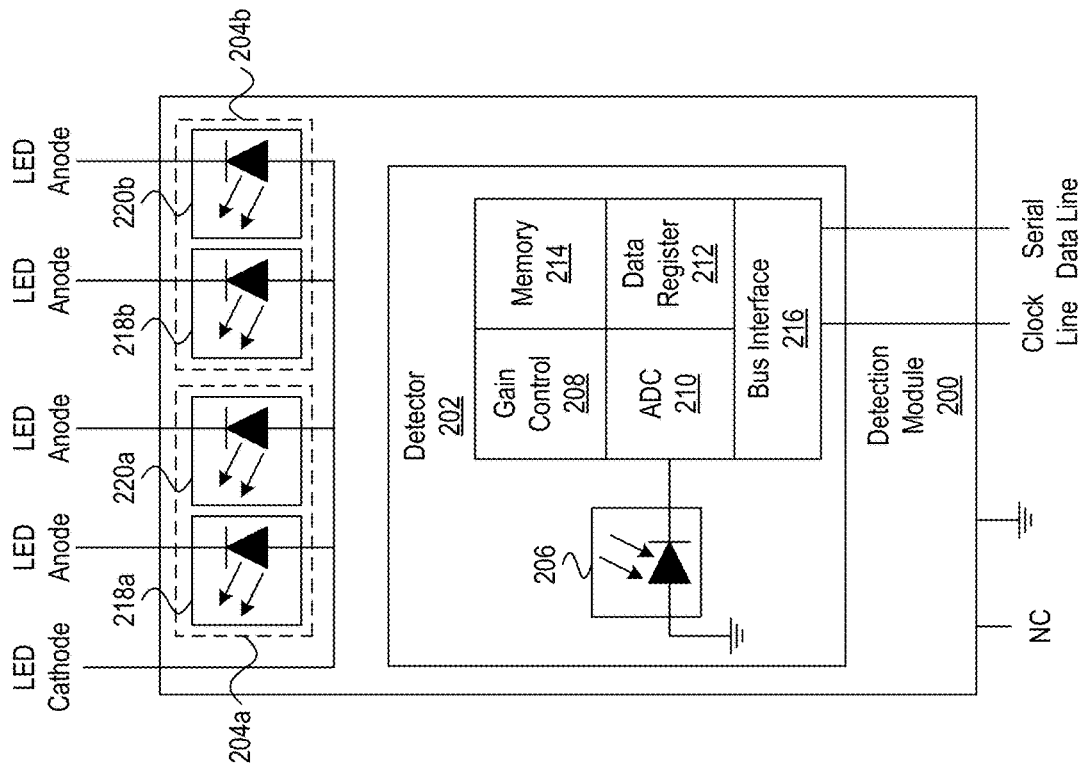
FIG. 2 is a block diagram of an example of an implementation of a detection module of a heart rate monitor in accordance with various aspects of the present disclosure.

A heart rate monitor is provided that may be worn by an individual, and the heart rate monitor may, in operation, determine a heart rate for the individual. According to some aspects of the disclosure, the heart rate monitor may be an optical heart rate monitor that measures heart rate based on the scattering of light through the skin of the individual as blood flows beneath the skin. The scattering of light through the skin of the individual may depend on whether blood is or is not present beneath the skin. Accordingly, the scattering of light through the skin of the individual may change as blood flows beneath the skin due to the heart beat of the individual. The optical heart rate monitor may detect the change in the scattering of light and determine a heart rate for the individual based on this change. The optical heart rate monitor may function over a broad range of illumination intensities and in a variety of ambient lighting conditions.

It will be appreciated, however, that the position of the skin of the individual may change beneath an optical heart rate monitor worn by that individual as the individual moves. As a result, the position of the skin relative to the optical heart rate monitor may affect the optical input received at the optical heart rate monitor. Accordingly, accurate heart rate measurements may be obtained by compensating for the skin position of the individual when obtaining optical input with which to determine a heart rate for the individual. Compensating for the skin position of the individual may be achieved by obtaining optical feedback from the heart rate monitor.

The heart rate monitor uses photoplethysmographic techniques to determine the heart rate of an individual. The advantage of photoplethysmography (PPG) is that it does not require an electro-potential measurement on opposing sides of the heart (body). It thus can be placed in the more desirable locations other than the chest such as, for example, on the upper or lower arm or wrist even within the device on the wrist.

PPG may, however, come with its own set of challenges. The first challenge may relate to providing a device, such as a wrist-worn device, that is not uncomfortable to the wearer. A user may prefer a looser fit for a device around the wrist. As a result, the spacing between the sensor of the device and the surface of the skin may vary, e.g., as the wearer moves. Where the device includes an optical sensor, the variation in spacing between the device and the skin of the user may modulate the reflected light in manner similar to the spectral scattering that modulates the light due to the heart beat of the wearer. To address this challenge, a device may be designed such that the sensor is held firmly against the skin of the wearer when the device is worn.

The second challenge may relate to the variation caused by the movement of the wearer. Even with the sensor held firmly against the skin, variations unrelated to heart rate may appear in the measurement. This variation may result from the relative angle changes between the impinging light and the skin surface as the muscles underlying lift and twist the device. Mean changes in blood pressure may also shift the signal with motion. Local variation in skin pigmentation can move in and out of the field of view of the sensor during activity. All of these movement-induced sources of noise may require compensation in order to identify the variation in light that is solely the result of the heartbeat of the wearer.

The heart rate monitor described below performs motion compensation in order to lower the movement-induced noise and provide an accurate determination of heart rate. The heart rate monitor described below may also be configured such that it may be used with a "comfort fit" (as most people wear their watches), which may be preferable to an "elastic band" fit, which may hold the a sensor tight against the skin of the wearer as in exiting technologies.

The functional details of the heart rate monitor, including details directed towards compensating for the skin position of the individual, are provided below. Stated generally, some example implementations of the heart rate monitor may provide one or more light emitting diodes, photodiodes, amplifiers, integrating analog-to-digital converters (ADCs), accumulators, clocks, buffers, comparators, a state machine, and a bus interface. The photodiode may be responsive to electromagnetic radiation such as, e.g., infrared light. An integrating ADC may convert an amplified photodiode current into a digital signal. Upon completion of a conversion cycle, the conversion result may be transferred to a data register. The result may thus represent an amount of electromagnetic radiation reflected off the skin of the user and detected at the photodiode. The digital output may be read by a microprocessor through which motion compensation may be applied resulting in an approximate heart rate for an individual.

In the following description of various example implementations, reference is made to the accompanying drawings, which form a part hereof, and in which are shown by way of illustration various example devices, systems, and environments in which aspects of the disclosure may be practiced. It is to be understood that other specific arrangements of parts, example devices, systems, and environments may be utilized and that structural and functional modifications may be made without departing from the scope of the present disclosure. Also, while the terms "top," "bottom," "front," "back," "side," and the like may be used in this specification to describe various example features and elements, these terms are used herein as a matter of convenience, e.g., based on the example orientations shown in the figures. Nothing in this specification should be construed as requiring a specific three dimensional orientation of structures in order to fall within the scope of the disclosure. Moreover, various aspects of the disclosure may be implemented using instructions stored on computer-readable media. As used in this disclosure, computer-readable media includes all computer-readable media with the sole exception being a transitory propagating signal.

Figure 1:
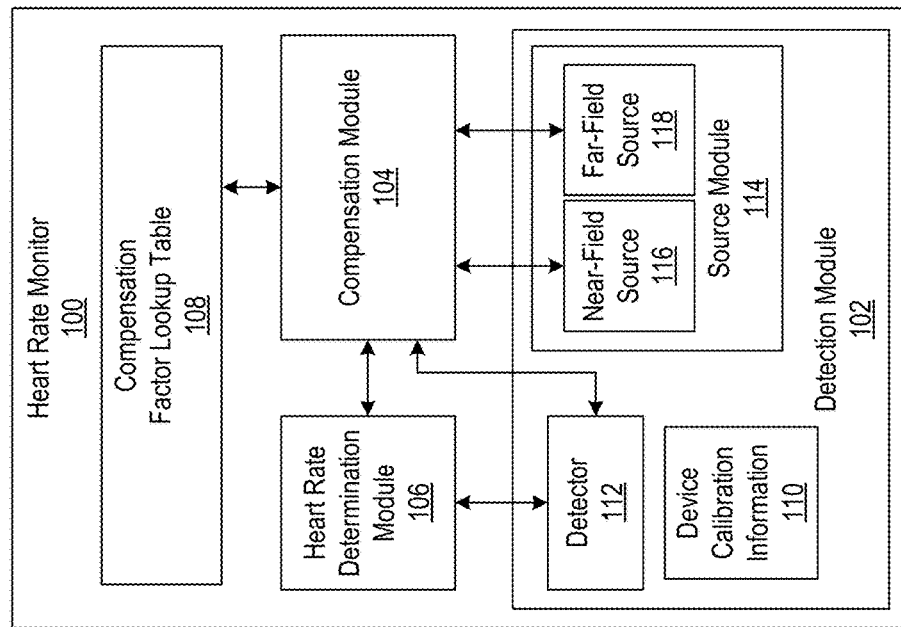
FIG. 1 is a block diagram of an example of an implementation of a heart rate monitor in accordance with various aspects of the present disclosure.

In FIG. 1 a block diagram of an example of an implementation of a heart rate monitor 100 in accordance with various aspects of the present disclosure is shown. The heart rate monitor 100, in this example, includes a detection module 102; a compensation module 104; a heart rate determination module 106; a compensation factor lookup table 108; and memory storing device calibration information 110. The detection module 102, in this example, includes a detector 112 and a source module 114. The source module 114, in this example, includes a near-field source 116 and a far-field source 118. As discussed in further detail below, a detection module of a heart rate monitor may include multiple source modules where each source module respectively includes a near-field source and a far-field source.

The near-field source 116 and the far-field source 118 may be, in some example implementations, light-emitting diodes. In other example implementations, the near-field source 116 and the far-field source 118 may be implemented using alternative types devices that generate electromagnet radiation. The electromagnetic radiation may be, for example, in the visible or infrared (IR) spectrum. In further example implementations, the near-field source 116 and the far-field source 118 may be implemented using devices that generate acoustic waves or other forms of energy suitable to monitor heart rate or determine a distance of a device from a surface, such as the distance between a wrist-worn device and the wrist of an individual wearing the wrist-worn device.

The compensation module 104 may identify a compensation factor to use when determining a heart rate for an individual. As described in further detail below, the compensation module 104 may identify a compensation factor based upon one or more ratios calculated from the output of the detector 112 of the detection module 102. The compensation factor lookup table 108 may store the compensation factors. The compensation factors stored in the compensation factor lookup table 108 may respectively correspond to a particular position of the skin of the user wearing the heart rate monitor 100. As described in further detail below, the compensation factors of the compensation factor lookup table 108 may be associated with one or more count value ratios. The compensation module 104 may perform a lookup of the compensation factor lookup table 108 using one or more count value ratios. The compensation module 104 may thus retrieve the compensation factor of the compensation factor lookup table 108 that is associated with the one or more count value ratios provided. Count value ratios will be discussed in further detail below.

The compensation factor may be applied when determining a heart rate in order to compensate for the skin position of an individual wearing the heart rate monitor 100. In some example implementations, the compensation module 104 may apply the compensation factor to the output of the detector 112 of the detection module 102. Alternatively, in other example implementations, the compensation module 104 may provide the compensation factor to the heart rate determination module 106, and the heart rate determination module may process the output received from the detector 112 using the compensation factor in order to accurately determine a heart rate for the individual. The heart rate determination module 106 and the compensation module 104 may be implemented using hardware, software, or a combination of hardware and software. In some example embodiments, the heart rate determination module 106 and the compensation module 104 may be implemented using a microprocessor programmed to perform one or more of the functions described below. The heart rate monitor 100 may also include a controller (not shown) such as, e.g., a microprocessor. As discussed further below, the microprocessor may be used to determine the heart rate of the individual.

In FIG. 2, a block diagram of an example of an implementation of a detection module 200 of a heart rate monitor (e.g., heart rate monitor 100 of FIG. 1) in accordance with various aspects of the present disclosure is shown. The detection module 200, in this example, includes a detector 202 and two source modules 204a and 204b. The detector 202, in this example, includes an illumination sensor 206, a gain control 208, an analog-to-digital converter 210, a data register 212, a memory 214, and a bus interface 216. The source modules 204a and 204b may each include two illumination sources, a near-field illumination source and a far-field illumination source. In FIG. 2, for example, the source module 204a includes a near-field illumination source 218a and a far-field illumination source 220a, and the source module 204b includes a near-field illumination source 218b and a far-field illumination source 220b.

In some example implementations, the near-field illumination sources 218a-b and far-field illumination sources 220a-b may be light-emitting diodes (LEDs). Accordingly, the near-field illumination sources 218a-b may be referred to as near-field LEDs, and the far-field illumination sources 220a-b may be referred to as far-field LEDs. The near-field LEDs 218a-b may be utilized to illuminate the skin of an individual wearing the device when the skin is positioned relatively close to the detector 202, e.g., when the skin of the individual is in the near-field region. The far-field LEDs 220a-b may be utilized to illuminate the skin of the individual when the skin is positioned relatively far from the detector 202, e.g., when the skin of the individual is in the far-field region. The near-field LEDs 218a-b and the far-field LEDs 220a-b may be configured to emit IR illumination.

The anodes of the LEDs 218a-b and 220a-b may be individually connected to a voltage source such that each LED is individually drivable from its respective voltage source (not shown). The cathodes of the LEDs 218a-b and 220a-b may be commonly connected to a current sink (not shown), and the anodes of the LEDs may be individually connected to general purpose input/output pins of a microprocessor (not shown), which may individually drive the LEDs.

The illumination sensor such as the illumination sensor 206 may, in some example implementations, be a photodiode that detects illumination from the near-field LEDs 218a-b and far-field LEDs 220a-b. The illumination detected by the photodiode 206 may include illumination that reflects off the skin of an individual. As the near-field LEDs 218a-b and far-field LEDs 220a-b may be configured to emit IR illumination, the photodiode 206 may be configured to detect the IR illumination. The photodiode 206, due to its construction, may be responsive to both IR illumination and illumination in the wavelength range of visible light. It has been observed that ambient visible light superimposed with IR illumination may include frequency spectra similar to that of the bulk scatter of light during a heartbeat. In order to combat this effect, the detector 202 may include an optical filter that blocks illumination in the wavelength range of visible light. As a result, the photodiode 206 may receive the IR illumination and not receive the visible light. The photodiode 206 may convert the IR illumination received into an analog current signal. The photodiode 206 may provide the analog current signal to the ADC 210

The ADC 210 may be an integrating ADC that converts the analog current signal received from the photodiode 206 into a digital output. When the LEDs 218a-b or 220a-b are illuminated, the integration may be initiated. upon completion of the conversion cycle, the output of the ADC may be stored in the data register 212, and the LEDs may be deactivated. The analog current signal received from the photodiode 206 may be amplified before converting the analog signal into a digital output. The data register 212 may store the value of the digital output. To ensure data integrity, transfers to the data register 212 may be double-buffered.

The digital output value may be read from the data register 212 via the bus interface 216 and provided to, e.g., a microprocessor of the heart rate monitor. The photodiode 206 may be referred to as a channel, and the output of the photodiode may be referred to as a channel count. The analog current signal provided by the photodiode 206 may correspond to the channel count, and the analog current signal may be converted into a digital value by the ADC 210 and stored at the data register 212.

The ADC 210 may provide digital output having up to 16 bits of resolution, and the integration time may impact both the resolution and the sensitivity of the reading from the photodiode 206. The integration time for one integration cycle may be 136 microseconds (μs). Additionally, the ADC 210 may be configured to perform up to 256 integration cycles.

The gain control 208 may control the amount of gain of the current signal from the photodiode 206. The gain control 208 may be programmed to provide gain of, e.g., 1×, 8×, 16×, or 120×. The memory 214 may be, e.g., flash memory and store manufacturing information and calibration information such as the device calibration information 110 discussed above with reference to FIG. 1. A microprocessor may access the information stored at the memory 214 via the bus interface 216.

The bus interface 216 may be, e.g., an I²C serial-compatible interface, standard or fast mode that access a set of registers (not shown) of the heart rate monitor. The I²C bus may be available from NXP Semiconductors N.V. headquartered in Eindhoven, The Netherlands. Additional and alternative types of busses and protocols may be selectively employed.

The registers may provide access to control functions and output data of the heart rate monitor. Some examples of the various registers that the heart rate monitor may provide include a command register; an enable register; an integration time register; a wait time register; a configuration register; a gain control register; an identification register; a status register; one or more data registers. The command register may specify the address of a target register for read or write operations. The enable register may be utilized to power the heart rate monitor on and off and enable various functions of the heart rate monitor. The enable register may, for example, be utilized to power on (PON) the heart rate monitor, enable the ADC 210 (AEN) of the heart rate monitor, and enable a wait timer (WEN) of the heart rate monitor that put the heart rate monitor into a wait state. The integration time register may be used to control the integration time of the ADC 210, e.g., in 136 μs increments. Accordingly, the integration time register may store a value corresponding to a desired number of integration cycles. The wait time register may store a wait time also in 136 μs increments, and the wait time register may store a value corresponding to a desired number of wait time increments.

The configuration register may store information used to scale the gain level and the wait time. Depending on the value stored in the configuration register, the gain level may, for example, be scaled by a factor of 0.16 or by a factor of 1. Also depending on the value stored in the configuration register, the wait time increment may be scaled by a factor of 12. The gain control register may provide a selected amount of gain to the ADC 210 of the heart rate monitor. The identification register may provide one or more values corresponding to a part number of the heart rate monitor. The status register may provide information regarding the internal status of the heart rate monitor. The status register may, for example, store a value corresponding to a cyclic redundancy check, which may be compared when writing information to memory of the heart rate monitor in order to determine validity of the information. The status register may also store a value that indicates the ADC 210 of the heart rate monitor has completed an integration cycle. The data register of the heart rate monitor, e.g., data register 212, may store the digital output from the ADC 210 as described above. The digital output provided by the ADC 210 may be stored in a data register as a 16-bit value. In some example implementations, multiple data registers may be employed, e.g., two data registers that store the digital output as two 16-bit values.

The heart rate monitor may support low-power modes including a sleep state, a wait state, and an active state. In the sleep state, only the resources used to detect a start condition at the bus interface 216 and used to check the enable register may be utilized. When the power management feature is enabled, a state machine of the heart rate monitor may transition to the wait state. The wait time may be determined by the values of the wait time register and the configuration register as described above. In the active state, the LEDs 218a-n and 220a-b may be activated to provide illumination. Also in the active state, the photodiode 206 may provide an analog current signal in response to illumination detected at the photodiode. Accordingly, the ADC 210 may also be activated in the active state in order to convert the analog current signal provided by the photodiode 206 to a digital output as described above. When the heart rate monitor is enabled, the state machine may transition through an initialization process to the active state. The time the heart rate monitor is in the active state may depend on the value stored in the integration time register.

An internal state machine may be utilized to control the active and wait features of the heart rate monitor. At power up, an internal power-on-reset may initialize the heart rate monitor and place the heart rate monitor in the low-power sleep state. When a start condition is detected at the bus interface 216, the heart rate monitor may transition to an idle state and check the enable register. If enable register indicates the heart rate monitor is disabled, the heart rate monitor may return to the sleep state to save power. Otherwise, the heart rate monitor may remain in the idle state until the enable register indicates the heart rate monitor is enabled. Once enabled, the heart rate monitor may carry out the wait states and active states in sequence as described above. Upon completion of a cycle and return to the idle state, the heart rate monitor may automatically begin a new wait-active cycle as long as the device remains powered on and enabled.

Figure 3A:
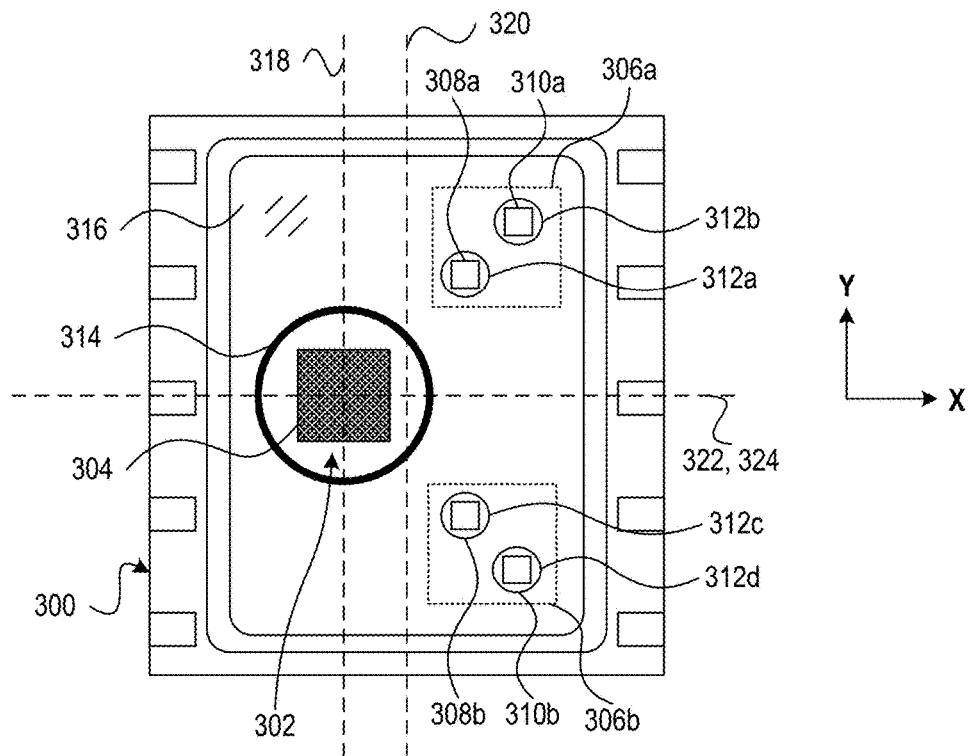
FIG. 3A is a plan view of an example of an implementation of a detection module of a heart rate monitor.
Figure 3B:
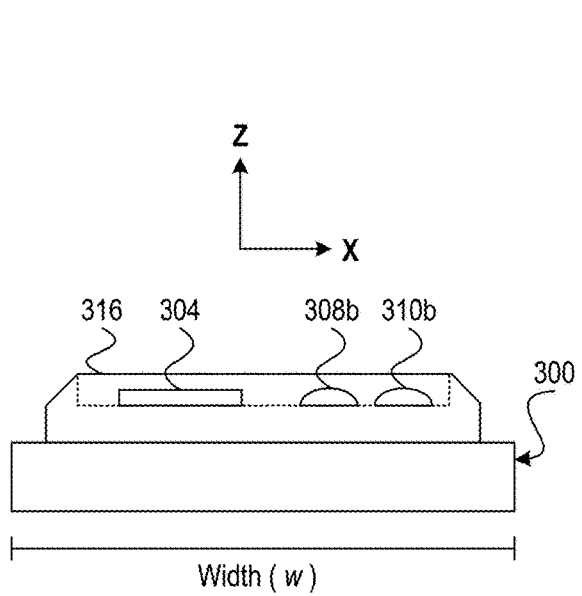
FIG. 3B is a front side view of the detection module of FIG. 3A.
Figure 3C:
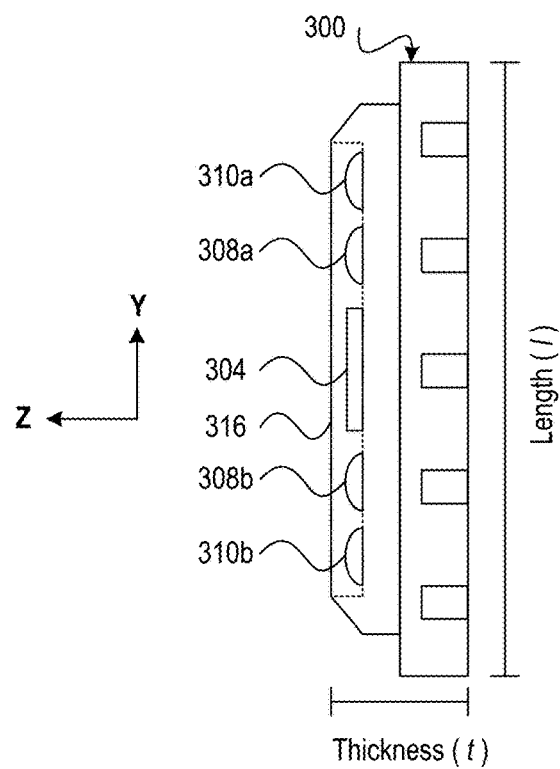
FIG. 3C is a lateral side view of the detection module of FIG. 3A.

Referring now to FIGS. 3A-B, an illustration of another example implementation of a detection module 300 of a heart rate monitor is shown. In FIG. 3A, a plan view of the detection module 300 of is shown. In FIG. 3B, a front side view of the detection module 300 is shown, and in FIG. 3C, a lateral side view of the detection module 300 is shown. In FIG. 3B and FIG. 3C, a cut-out of the detection module 300 is illustrated via respective dashed lines in order to illustrate various components of the detection module. It will be appreciated that the terms front side and lateral side are simply used for convenience and should not be construed to identify any particular side of the detection module 300.

The detection module 300 in FIGS. 3A-C may be similar to the detection module 200 described above with reference to FIG. 2. Accordingly, the detection module 300, in this example, includes an illumination sensor 302 having a photodiode 304 and two illumination source modules 306a and 306b. The illumination source module 306a may include a near-field LED 308a and a far-field LED 310a. The illumination source module 306b may likewise include a near-field LED 308b and a far-field LED 310b. The detection module 300 may also include respective lens elements that cover the LEDs 308a-b and 310a-b as well as the photodiode 304. The detection module 300, in this example, may include a lens element 312a that covers LED 308a, a lens element 312b that covers LED 310a, a lens element 312c that covers LED 308b, and a lens element 312d that covers LED 310b. The detection module 300 may also include a lens element 314 that covers the photodiode 304. In addition, the detection module 300, in this example, may include a window 316 across the face of the detection module that protects the various components of the detection module. Lens elements will be discussed in further detail below.

As also shown by way of example in FIG. 3A, a centerline 318 of the photodiode 304 along the Y-axis may be offset from the centerline 320 of the detection module 300 along the Y-axis. The centerline 322 of the photodiode 304 along the X-axis, however, may be collinear with the centerline 324 of the detection module 300 along the X-axis in this example. As also shown by way of example in FIG. 3A, the LEDs 308a-b and the LEDs 310a-b are positioned at an oblique angle relative to the centerlines 318 and 322 of the photodiode 304. The LEDs 308a-b and 310a-b, in this example, are positioned at about a 45° angle relative to the centerlines 318 and 322 of the photodiode 304. It will thus be appreciated that a line extending through LEDs 308a and 310a and a line extending through LEDs 308b and 310b and intersecting at the center of the photodiode 304 may be orthogonal relative to one another.

As seen in FIG. 3B and FIG. 3C, the detection module may have a width, w, a length, l, and a thickness, t. In some example implementations, the width, w, of the detection module 300 may be about 10 mm; the length, l, of the detection module may be about 12 mm; and the thickness, t, of the detection module may be about 5 mm. It will be appreciated that the dimensions of the detection module 300 may depend on various design constraints that arise during various implementations of the detection module. Accordingly, alternative implementations of the detection module may exhibit alternative dimensions.

The face of the detection module 300 may be positioned against the skin of an individual when the individual wears a heart rate monitor that incorporates the detection module. The position of the skin relative to the face of the detection module 300 may be described in terms of a translation, $\Delta Z$, along the Z-axis; a rotation, $\theta_X$, of a surface of the skin about the X-axis; and a rotation, $\theta_Y$, of the surface skin about the Y-axis. The translation, $\Delta Z$, may represent the distance between the face of the detection module 300 and the surface of the skin of the individual wearing the heart rate monitor. When the face of the detection module 300 is flat against the surface of the skin of the individual, the skin position may be referred to as the origin skin position and described as $\Delta Z=0$, $\theta_X=0°$, and $\theta_Y=0°$. When compensating for the skin position during the heart rate determination process, the skin position may be described relative to this origin skin position. The range of translation of the surface of the skin along the Z-axis (the "Z range") may, in some circumstances, range between about 0 mm ($Z_{min}$) and about 8.6 mm ($Z_{max}$). In addition, the rotation of the surface of the skin about the X-axis, $\theta_X$, may range between about −19.6° and about +19.6°; and the rotation of the surface of the skin about the Y-axis, $\theta_Y$, may range between about −31.4° and about +31.4°.

As described above, an accurate heart rate may be determined by compensating for the changes in illumination caused by the changes in the position of the skin of an individual as the individual moves while wearing the heart rate monitor. The heart rate monitor may compensate for the position of the skin of the individual by obtaining spatial feedback regarding the position of the skin of the individual. The spatial feedback may be obtained by measuring the ratio of the respective count values obtained when a near-field LED and a far-field LED of an illumination source module are illuminated, e.g., a count value, N, for the near-field LED 308a and a count value, F, for the far-field LED 310a of illumination source module 306a. A count value ratio, N/F, may be obtained for each of the source modules of a detection module, e.g., the source modules 306a and 306b of the detection module 300.

Figure 4A:
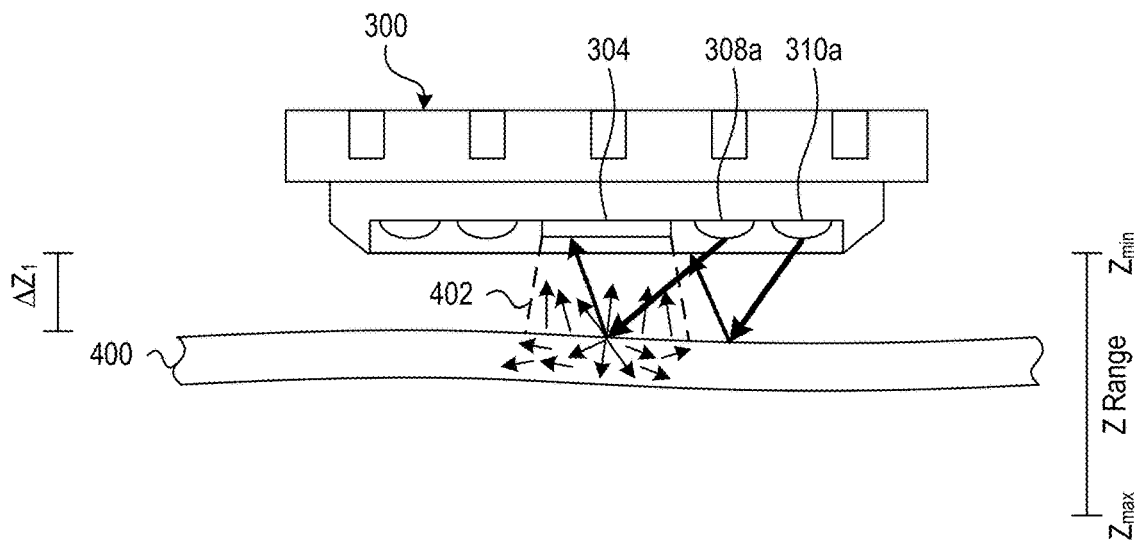
FIG. 4A is a lateral side view of the detection module of FIG. 3A positioned relative to the skin of an individual.
Figure 4B:
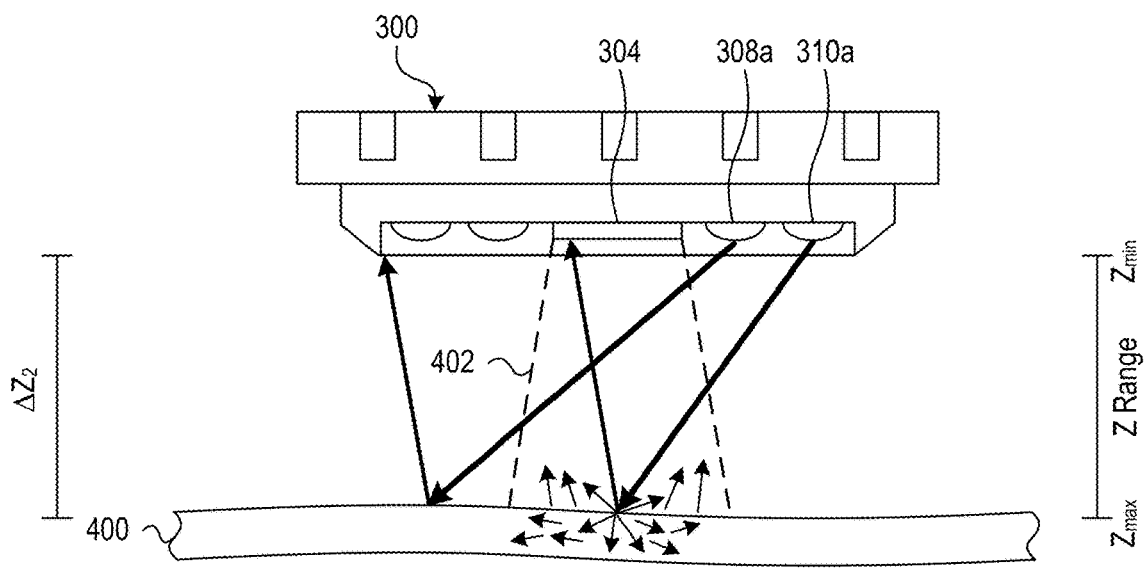
FIG. 4B is another lateral side view of the detection module of FIG. 3A positioned relative to the skin of an individual.

It will be appreciated that the count value for an LED may depend on the position of the surface of the skin of an individual wearing the heart rate monitor. Referring to FIGS. 4A-B, a lateral side view of the detection module 300 relative to the skin 400 of an individual is shown. In FIG. 4A the skin 400 of the individual is relatively close to the detection module 300. Stated differently, the translation of the skin 400 along the Z-axis, $\Delta Z_1$, is relatively small in FIG. 4A. In FIG. 4B the skin 400 of the individual is relatively far from the detection module 300. Stated differently, the translation of the skin 400 along the Z-axis, $\Delta Z_2$, is relatively large in FIG. 4B.

As seen in FIGS. 4A-B, the amount of illumination from the LEDs 308b and 310b that is detected by the photodiode 304 may depend on the position of the skin 400 relative to the detection module 300. As seen in FIG. 4A, for example, illumination from the near-field LED 308b may fall within the field-of-view (FOV) 402 of the photodiode 304 when the skin 400 is relatively close to the detection module 300, e.g., when $\Delta Z_1$ is relatively small. As also seen in FIG. 4A, most or all of the illumination from the far-field LED 310b may fall outside of the FOV 402 of the photodiode 304 when the skin 400 is relatively close to the detection module.

As a result, the photodiode 304 may detect illumination from the near-field LED 308b that falls within the FOV 402 and is reflected off the skin 400 when the skin is relatively close to the detection module 300. The photodiode 304 might not, however, detect most or all of the illumination from the far-field LED 310b that falls outside of the FOV 402 when the skin 400 is relatively close to the detection module 300. It will thus be appreciated that the count value, N, for the near-field LED 308b may be relatively high and the count value, F, for the far-field LED 310 may be relatively low (e.g., close to zero) when the skin 400 is relatively close to the detection module 300. Accordingly, the count value ratio, N/F, may approach infinity (N/F→∞) as the distance, $\Delta Z_1$, between the detection module 300 and the skin 400 decreases and the count value, F, for the far-field LED 310b approaches zero.

When the skin 400 is relatively far from the detection module 300, however, the illumination from the far-field LED 310b may fall within the FOV 402 of the photodiode 304 and illumination from the near-field LED 308a may fall outside the FOV 402 of the photodiode. As seen in FIG. 4B, for example, illumination from the far-field LED 310b may fall within the FOV 402 of the photodiode 304 when the skin 400 is relatively far from the detection module 300, e.g., when $\Delta Z_1$ is relatively large. As also seen in FIG. 4B, most or all of the illumination from the near-field LED 308b may fall outside of the FOV 402 of the photodiode 304 when the skin 400 is relatively far from the detection module.

As a result, the photodiode 304 may detect illumination from the far-field LED 310b that falls within the FOV 402 and is reflected off the skin 400 when the skin is relatively far from the detection module 300. The photodiode 304 might not, however, detect most or all of the illumination from the near-field LED 308b that falls outside of the FOV 402 when the skin 400 is relatively far from the detection module 300. It will thus be appreciated that the count value, N, for the near-field LED 308b may be relatively low (e.g., close to zero) and the count value, F, for the far-field LED 310 may be relatively high when the skin 400 is relatively far from the detection module 300. Accordingly, the count value ratio, N/F, may approach zero (N/F→0) as the distance, $\Delta Z_1$, between the detection module 300 and the skin 400 increases and the count value, N, for the near-field LED 308b approaches zero.

A count value ratio, N/F, may be calculated for each illumination source module of a detection module. With reference to the detection module 300 described above, a first count value ratio, $N_1/F_1$, may be calculated for the source module 306a based on a count value, $N_1$, obtained for illumination from the near-field LED 308a and a count value, $F_1$, obtained for illumination from the far-field LED 310a. Similarly, a second count value ratio, $N_2/F_2$, may be calculated for the source module 306b based on a count value, $N_2$, obtained for illumination from the near-field LED 308b and a count value, $F_2$, obtained for illumination from the far-field LED 310b. The compensation module (e.g., compensation module 104) may thus use this pair of count value ratios, $N_1/F_1$ and $N_2/F_2$, to identify a skin position by performing a lookup in a compensation factor lookup table such as the compensation factor lookup table 108 described above with reference to FIG. 1.

The optical design of the detection module 300 creates a modulation of the photocurrent that depends on the spatial orientation of the detection module with respect to the surface of the skin of the individual. When the surface of the skin is near the window 316, the illumination from the far-field LEDs 310a-b is mostly or entirely outside the FOV 402 of the photodiode 304. The photocurrent provided by the photodiode 304 would therefore be near zero when the surface of the skin is near the window 316. In contrast, the illumination from the near-field LEDs 308a-b would result in a relatively high value of photocurrent from the photodiode 304 when the surface of the skin is near the window 316 since the illumination from the near-field LEDs would fall within the FOV 402 of the photodiode.

The photocurrent provided by a photodiode may also depend on the rotation of the detection module with respect to the surface of the skin of the individual. In example implementations having a source module parallel to the X-axis, the amount of illumination detected at a photodiode from this source module may remain constant as the detection module is rotated about the X-axis. The amount of illumination detected by the photodiode from the other source module, which may be positioned orthogonal to the X-axis, may decline rapidly as the rotation about the X-axis increases in magnitude. When the detection module is rotated about the Y-axis as similar effect may be observed for a source module positioned parallel with the Y-axis and a source module positioned orthogonal to the Y-axis. Compound rotation about the X-axis and the Y-axis may produce a response that is a convolution of the illumination from both source modules. Example implementations that include respective source modules parallel to the X-axis and Y-axis are discussed further below with reference to FIGS. 7A-C.

A heart rate monitor may obtain spatial feedback by measuring the ratio of the current values obtained using the near-field LED and far-field LED of each source module, in other words, by illuminating the LEDs of the left source module and the right source module. The near-field LED and the far-field LED of a source module may illuminated one at a time. The ADC provides a count value corresponding to the current provided by the photodiode. The count values may then be stored for further processing and analysis. Each of the measured values may be divided by a reference value to obtain a normalized ratio. The denominator of the normalized ratio may be the count value resulting from illumination by any one of the LEDs. The reference value may, in some example implementations, be the photocurrent measured when two or more of the LEDs are illuminated. The reference value may, for example, be the current measured when both near-field LEDs are simultaneously illuminated, $N_1$ and $N_2$. Using this example, the ratios may be $N_1/(N_1+N_2)$, $N_2/(N_1+N_2)$, $F_1/(N_1+N_2)$, $F_2/(N_1+N_2)$. Since the relationship between intensity of the illumination may be linear with respect to photocurrent, the ratio may be unaffected by the absolute level of intensity of each LED.

The spatial feedback corresponding to the orientation of a detection module with respect to the skin may be determined by comparing the calculated ratio to ratios contained in a compensation lookup table as described above. The ratios contained in the compensation lookup table may be equated directly to a known orientation. The sum of the least square difference between the calculated ratio and the ratios contained in the compensation lookup table may be used to identify the orientation of the compensation lookup table that best matches the present orientation of the detection module.

The raw signal for determining heart rate may come from two sources: the photocurrent with each near-field LED illuminated (the "near signal") and the photocurrent with each far-field LED illuminated (the "far signal"). For each orientation contained in the compensation lookup table, there may be a scaling factor for the near signal and the far signals. The scaling factors may be derived by characterizing the average signal magnitude at a particular orientation and dividing it by the average signal magnitude at a nominal orientation such as, e.g., $\Delta Z=2.8$ mm, $\theta_X=0$, and $\theta_Y=0$.

With the actual orientation of the detection module determined, the count value measured for the near signal may be multiplied by a near-field scaling factor and then stored as a spatially-compensated raw data value. Likewise the count value for the far signal may be multiplied by a far-field scaling factor and then also stored as the spatially-compensated raw value.

The entire data sampling sequence of $N_1$; $N_2$; $N_1$ and $N_2$; $F_1$; $F_2$; and $F_1$ and $F_2$ may be repeated about 30-128 times per second. To save power, the spatial compensation may only be applied at a much lower sample interval with only $N_1$, $N_2$, $F_1$, and $F_2$ being illuminated singularly once every four measurements of the samples from $N_1$ and $N_2$; and $F_1$ and $F_2$.

The spatial compensation may depend on spatial feedback from the detection module and may represent only one aspect of the entire compensation process for motion. Additional feedback provided by ancillary sensors such as accelerometers or gyrometers may also be incorporated to further cancel motion-induced noise in the raw signals.

The particular positioning of the near-field LEDs and far-field LEDs within a detection module may affect the sensitivity of the N/F ratio as well as the Z range over which illumination from the LEDs falls within the FOV of a photodiode. It will be appreciated that the angle of incidence of the illumination from the LEDs increases as the LEDs move farther out from the photodiode. As the LEDs move farther out from the photodiode, the sensitivity of the N/F ration may increase, but the Z range may decrease. A suitable position for the near-field LEDs and far-field LEDs relative to the photodiode may be one in which illumination is provided over an identified Z range while retaining a response for the N/F ratio.

The lens elements that cover the :LEDs of the detection module may focus the illumination provided by the LEDs such that the maximum amount of reflected illumination is achieved at a particular distance, $\Delta Z$, along the Z-axis. In some implementations, for example, a lens element for a near-field LED may focus illumination from the near-field LED such that the maximum amount of reflected illumination is achieved when $\Delta Z=2.8$ mm, $\theta_X=0°$, and $\theta_Y=0°$. In some implementations, as another example, a lens element for a far-field LED may focus illumination from the far field LED such that the maximum amount of reflected illumination is achieved when $\Delta Z=5.6$ mm, $\theta_X=0°$, and $\theta_Y=0°$. Furthermore, the near-field LEDs and far-field LEDs may be positioned off-center relative to their respective lens elements to produce an illumination distribution in which peak illumination occurs non-orthogonal relative to the face of the detection module. Additional and alternative configurations will be appreciated with the benefit of this disclosure.

It will also be appreciated with the benefit of this disclosure that various tolerances for the components of a detection module may lead to slightly different N/F ratios from individual detection modules. As an example, the placement tolerances of the LEDs, and the molding and positioning tolerances of the lens elements may contribute to variations in the N/F ratio at given distances, $\Delta Z_n$, along the Z-axis. To compensate for these variations across individual detection modules, a heart rate monitor may have its response measured during testing in order to determine unique calibration information for the heart rate monitor. The calibration information may be stored at the heart rate monitor (e.g., as device calibration information 110) and utilized when determining the heart rate of an individual wearing the heart rate monitor.

In some example implementations, more than one detector or photodiode. For example, multiple detectors may be positioned around a wrist-worn device, and one of the detectors may be selected for measuring heart rate at a given time based upon the N/F ratio associated with that detector. For example, the detector associated with an N/F ratio indicating that detector is the closest detector to the skin may be used to obtain the compensation factor used when determining the heart rate. Stated more generally, the detector associated with an N/F ratio indicating that detector is positioned such that it is likely to produce a signal corresponding to the most accurate heart rate may be used. The detector selected may vary over time as the device moves.

For the purposes of illustration, two pairs of LEDs representing near-field and far-field sources are shown. Additional LEDs may also be used as near-field and far-field sources. In some example implementations, a single pair of LEDs may be used as the near-field and far-field source. In some example implementations, the near-field and far-field sources may be associated with multiple detectors. For example, a single pair of near-field and far-field sources may be positioned between multiple detectors and used with those detectors simultaneously or independently. Alternative implementations of the heart rate monitor may include other types of sensors for determining skin position (e.g., distance) relative to the device. For example, a temperature sensor may be used in some example implementations. Accelerometers, gyrometers, and other types of sensors may be used to sense various parameters that may be used to obtain compensation factors.

Figure 5:
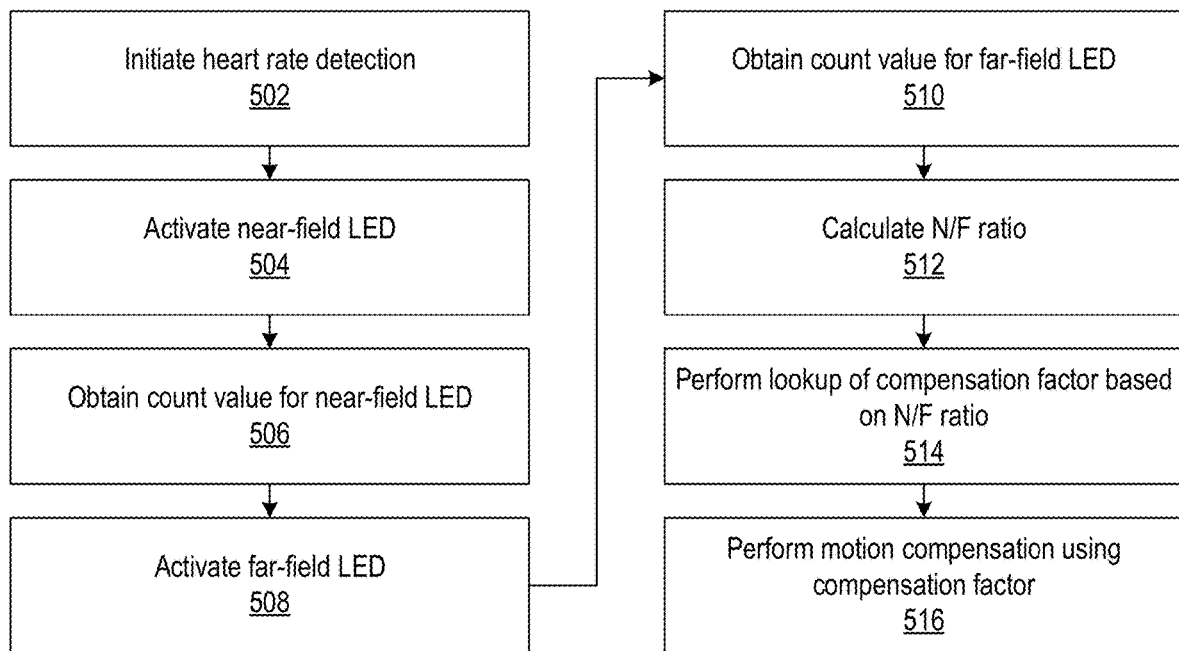
FIG. 5 is a flowchart of example method steps for determining a heart rate using a heart rate monitor.

In FIG. 5, a flowchart 500 of example method steps for determining a heart rate using a heart rate monitor is shown. The heart rate determination process may be initiated (block 502), and the near-field LED may be activated (block 504). A count value, N, for the near-field LED may be obtained (block 506), e.g., using a photodiode and an ADC as described above. The far-field LED may then be activated (block 508), and a count value, F, for the far-field LED may also be obtained (block 510), e.g., using the photodiode and the ADC as also described above. The ratio of N to F, the N/F ratio, may be calculated (block 512), and a lookup may be performed using the N/F ratio (block 514), e.g., at a compensation factor lookup table as described above. The compensation factor may be provided to a heart rate determination module using the compensation factor (block 516) in order to account for the position of the skin of the user. It will be appreciated that steps 504-512 may be performed for each source module of the detection module of a heart rate monitor.

Figure 6:
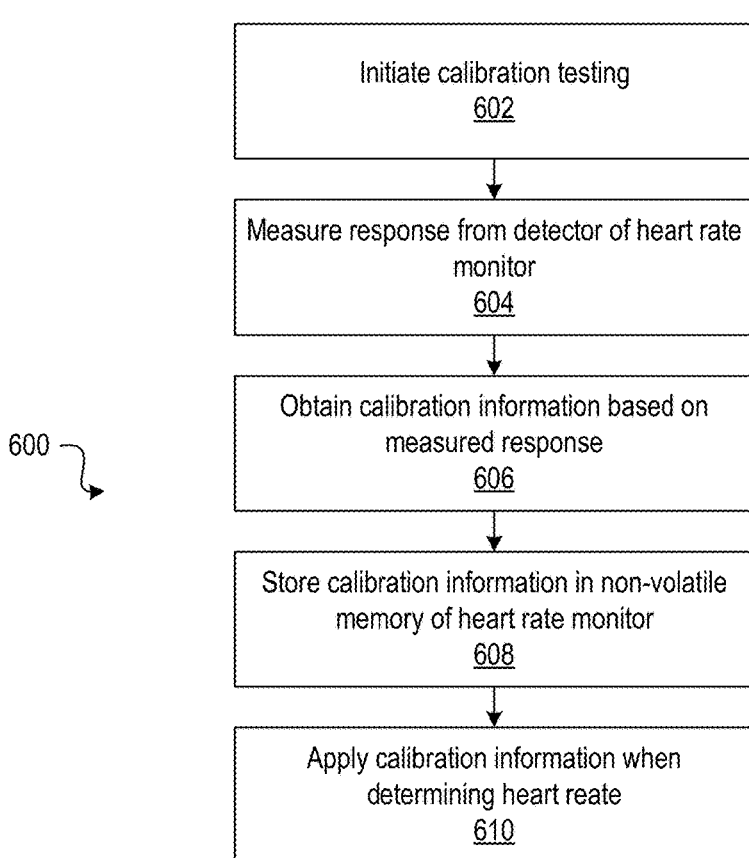
FIG. 6 is another flowchart of example method steps for determining a heart rate using a heart rate monitor.

In FIG. 6, another flowchart 600 of example method steps for determining a heart rate using a heart rate monitor is shown. As noted above, various tolerances in the manufacturing of the heart rate monitor may result in variable N/F ratios across individual heart rate monitors. Accordingly, a calibration process may identify calibration information that each heart rate monitor may utilize when determining a heart rate for an individual. The calibration process may be initiated (block 602) for a heart rate monitor, and the response from the detector of the detection module of the heart rate monitor may be measured (block 604). Based on the measured response from the detector, calibration information may be obtained for the heart rate monitor (block 606). The calibration information may be stored in non-volatile memory of the heart rate monitor (block 608), and the heart rate determination module of the heart rate monitor may apply the calibration information when determining a heart rate for an individual (block 610).

In FIGS. 7A-C, a perspective view of another example of an implementation of a detection module 700 of a heart rate monitor is shown. The detection module 700 may include features similar to that of the detection module 300 described above with reference to FIGS. 3A-C. The detection module 700 in this example, however, illustrates an alternative configuration for the illumination detector 702 and the source modules 704a and 704b. The source modules 704a and 704b may likewise include a respective near-field illumination source 706a and 706b and a respective far-field illumination source 708a and 708b. As shown by way of example in FIG. 7A, the illumination detector 702 may be a photodiode, and the illumination sources 706a-b and 708a-b may be LEDs. The detection module 700 may also include a controller 710, e.g., a microprocessor. The photodiode 702 and the LEDs 706a-b and 708a-b may be connected to the microprocessor 710 as described above. Additionally, the microprocessor 710, photodiode 702, and LEDs 706a-b and 708a-b may be positioned on a substrate 712 of the detection module 700.

As seen in FIG. 7A, the photodiode 702 is positioned off-center of the substrate 712 proximate to one of the corners of the substrate. The source modules 704a and 704b, in this example, are positioned in line with the photodiode 702 and orthogonal relative to one another. As shown in FIG. 7A, a centerline 714 passing through the source module 704a intersects a centerline 716 passing through the source module 704b at the center of the photodiode 702 such that the centerlines 714 and 716 are perpendicular relative to one another. As noted above, the LEDs may be configured to provide IR illumination or visible light illumination. Accordingly, in some example implementations, the LEDs may exhibit a peak wavelength of around 590 nanometers (nm), which corresponds to amber-colored visible light. In other example implementations, the LEDs may exhibit other wavelengths such as, e.g., around 560 nm, which corresponds to green-colored visible light.

As noted above, respective lens elements may cover the illumination detector and the illumination sources. Referring to FIG. 7B, the detection module 700 may include multiple lens components 718 and 720a-b. The lens component 718 may cover the photodiode 702 and include a lens element 722. The lens component 720a may cover the illumination source module 704a and include lens elements 724a and 724b. The lens element 724a may cover the near-field LED 706a, and the lens element 724b may cover the far-field LED 708a. Similarly, the lens component 720b may cover the source module 704b and include lens elements 724c and 724d. The lens element 724c may cover the near-field LED 706b, and the lens element 724d may cover the far-field LED 708b.

As shown by way of example in FIG. 7B, the lens elements 724a-d may exhibit a hemispherical shape. The lens elements 724a-d may thus focus the illumination respectively provided by the LEDs 706a-b and 708a-b on the skin of an individual wear a heart rate monitor that incorporates the detection module. As an example, the lens elements 724a and 724c may focus the illumination from the respective near-field LEDs 706a and 706b such that the amount of illumination reflected of the skin of the individual and returned to the photodiode 702 is maximized when the skin is at a distance of about 2.8 mm from the face of the detection module 700. As another example, the lens elements 724b and 724d may focus the illumination from the respective far-field LEDs 708a and 708b such that the amount of illumination reflected of the skin of the individual and returned to the photodiode 702 is maximized when the skin is at a distance of about 5.6 mm from the face of the detection module 700. As also shown by way of example in FIG. 7B, the lens element 722 may exhibit a cylindrical shape. The lens element 722 may thus serve as a light pipe utilizing total internal reflection to capture illumination reflected off the skin of an individual and returned to the photodiode 702 even when the illumination may be off-center relative to the lens element.

The lens elements 722 and 724a-d may be formed of thermoplastic epoxy in a transfer mold process. Slots 726 may separate the respective areas around the illumination detector 702, the source modules 704a and 704b, and the microprocessor 710. The slots 726 function to provide a space into which an optically opaque thermoplastic elastomer covering can be formed. In FIG. 7C, the detection module 700 is shown with an optically opaque thermoplastic elastomer covering 728 attached. The covering 728 includes openings to expose the lens elements 722 and 724a-d.

The heart rate monitor provided in this disclosure may be well-suited for use in wrist-worn portable devices such as sport watches, activity monitors, portable media players, and other types of device worn by an individual. The optical heart rate monitor may also be well-suited for devices where low power consumption is desired and where a determination of heart rate via electrocardiography is unavailable or otherwise not desired.

Figure 8:
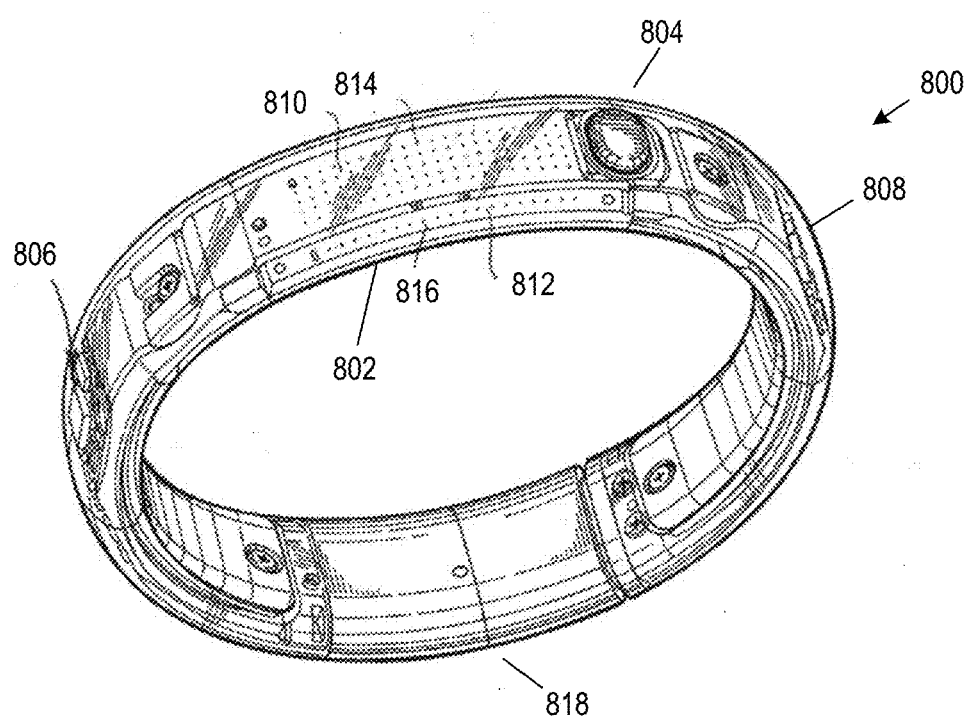
FIG. 8 is a perspective view of an example of an implementation of a device that may incorporate a heart rate monitor.

One such device for which the heart rate monitor is well suited includes the wrist-worn device 800 shown in FIG. 8. A heart rate monitor such as those described above may be incorporated into the wrist-worn device 800. The heart rate monitor may be located in the wrist-worn device 800 such that the face of the detection module of the heart rate monitor faces the skin of an individual when the individual is wearing the wrist-worn device. In some example implementations, the heart rate monitor may be located at the underside 802 of the wrist-worn device 800 near the top of the wrist-worn device such that the face of the detection module faces downward toward the top of the wrist of the individual. Other locations for the heart rate monitor may be selectively employed.

The wrist-worn device 800 may include an input mechanism, such as a depressible input button 804 to assist in operation of the device. The input button 804 may be operably connected to a controller 806 or other electronic components, such as one or more of the elements discussed below with reference to FIGS. 9-11. The controller 806 may be embedded or otherwise part of housing 808. The housing 808 may be formed of one or more materials, including elastomeric components and comprise one or more displays, such as display 810. The display 810 may be considered an illuminable portion of the wrist-worn device 800. The display 810 may include a series of individual lighting elements or light members such as LED lights. The lights may be formed in an array and operably connected to the controller 806. The wrist-worn device 800 may include an indicator system 812, which may also be considered a portion or component of the overall display 810. The indicator system 812 may operate and illuminate in conjunction with the display 810 (which may have multiple pixel members 814) or completely separate from the display 810. The indicator system 812 may also include a plurality of additional lighting elements or lighting members 816, which may also take the form of LED lights in one example implementation. In some example implementations, the indicator system 812 may provide a visual indication of goals, such as by illuminating a portion of lighting members 816 to represent accomplishment towards one or more goals.

A fastening mechanism 818 can be disengaged wherein the wrist-worn device 800 can be positioned around a wrist or other portion of an individual. Once positioned on the individual, the fastening mechanism 818 may be subsequently placed in an engaged position. In some example implementations, the fastening mechanism 818 may comprise an interface, including but not limited to a USB port, for operative interaction with a computer or other devices, such as devices. In some example implementations, the fastening member may comprise one or more magnets. In some example implementations, the fastening member may be devoid of moving parts and rely entirely on magnetic forces.

In some example implementations, the wrist-worn device 800 may comprise a sensor assembly (not shown). The sensor assembly may comprise a plurality of different sensors, including those disclosed herein or known in the art. In an example implementation, the sensor assembly may comprise or permit operative connection to any sensor disclosed herein or known in the art. The wrist-worn device 800 may be configured to receive data obtained from one or more external sensors as well. The wrist-worn device 800 may be configured to display data expressed in terms of activity points or currency earned by an individual based on the activity of the individual.

Figure 9:
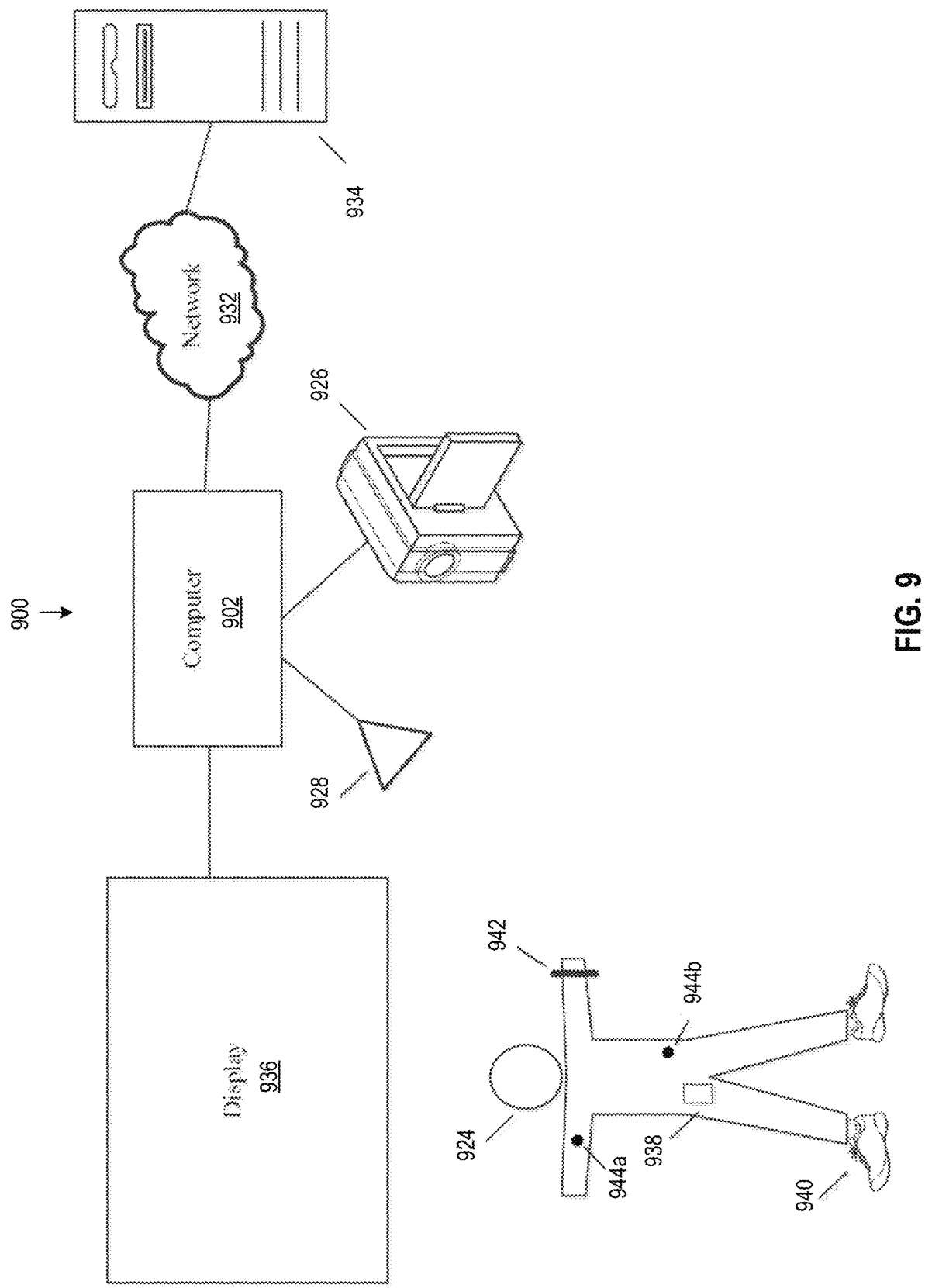
FIG. 9 is block diagram of an example of an implementation of a system for monitoring the movements of a user.

Referring now to FIG. 9, an example of a personal training system 900. The system 900 may include one or more electronic devices, such as computer 902. The computer 902 may comprise a mobile terminal, such as a telephone, music player, tablet, netbook or any portable device. In some example implementations, the computer 902 may comprise a media player or recorder, desktop computer, server(s), a gaming console, such as for example, a Microsoft® XBOX, Sony® Playstation, or a Nintendo® Wii gaming consoles. It will be appreciated that these are merely example devices for descriptive purposes and this disclosure is not limited to any particular console or type of computing device.

Figure 10:
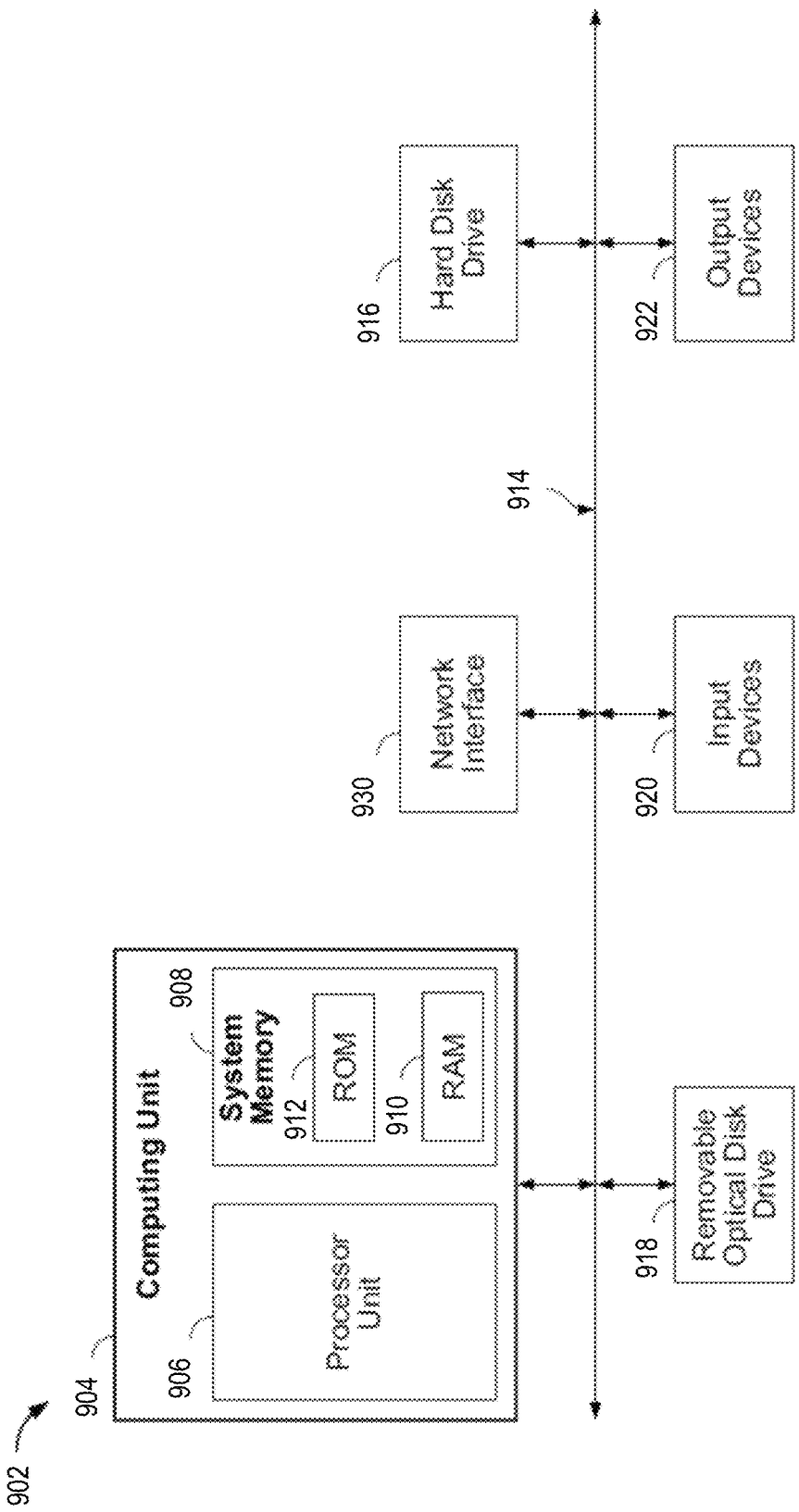
FIG. 10 is a block diagram of an example of an implementation of a computer of the system of FIG. 9.

Turning briefly to FIG. 10, the computer 902 may include a computing unit 904, which may comprise at least one processor unit 906. Processor unit 906 may be any type of processing device configured to execute software instructions, such as for example, a microprocessor device. The computer 902 may include a variety of non-transitory computer readable media, such as memory 908. The memory 908 may include, but is not limited to, random access memory (RAM) such as RAM 910; or read only memory (ROM), such as ROM 912. The memory 908 may include any one or more of: electronically erasable programmable read only memory (EEPROM), solid-state memory, optical or magnetic disk storage, or any other non-transitory medium that can be used to store electronic information.

The processor unit 906 and the memory 908 may be connected, either directly or indirectly, through a bus 914 or alternate communication structure to one or more peripheral devices. For example, the processor unit 906 or memory 908 may be directly or indirectly connected to additional memory storage, such as hard disk drive 916, optical drive 918 or any other memory. The processor unit 906 and memory 908 also may be directly or indirectly connected to one or more input devices 920 and one or more output devices 922. The output devices 922 may include, for example, a display device 936 (FIG. 9), audio-visual equipment, tactile feedback mechanisms or other devices. In some example implementations, one or more display devices may be incorporated into eyewear and optionally configured to provide feedback to users. The input devices 920 may include, for example, a keyboard, touch screen, remote control pad, pointing device (such as a mouse, touchpad, stylus, trackball, or joystick), scanner, a camera, a microphone or any sensor disclosed herein. Example sensors and illustrative uses thereof are provided below. In this regard, input devices 920 may comprise one or more sensors configured to sense, detect, or measure athletic movement from a user, such as user 924, shown in FIG. 9.

Looking again to FIG. 9, image-capturing device 926 or sensor 928 may be utilized in detecting or measuring athletic movements of user 924. In some example implementations, data obtained from image-capturing device 926 or other sensors, such as sensor 928, may detect athletic movements, either directly (e.g., data may be directly correlated to a motion parameter) or indirectly (data may be utilized in combination, either with each other or with other sensors to detect or measure movements). Thus, certain measurements may be determined from combining data obtained from two or more devices. The computer 902 may also use touch screens or image capturing device to determine where a user is pointing to make selections from a graphical user interface. The image-capturing device 926 or sensor 928 may include or be operatively connected to one or more sensors, including but not limited to those disclosed herein.

The computer 902, the computing unit 904, or other electronic devices may be directly or indirectly connected to one or more network interfaces, such as example interface 930 (as shown in FIG. 10) configured to permit communication with a network, such as network 932 (FIG. 9). In the example of FIG.10, the network interface 930, may comprise a network adapter or network interface card (NIC) configured to translate data and control signals from the computing unit 904 into network messages according to one or more communication protocols, such as the Transmission Control Protocol (TCP), the Internet Protocol (IP), and the User Datagram Protocol (UDP). The network interface 930 may employ any suitable connection agent for connecting to a network 932. The network 932, however, may be any one or more information distribution network(s), of any type(s) or topology(s), alone or in combination(s), such as internet(s), intranet(s), cloud(s), LAN(s). The network 932 may be any one or more of cable, fiber, satellite, telephone, cellular, wireless, etc. and as such, be variously configured such as having one or more wired or wireless communication channels (including but not limited to: WiFi®, Bluetooth®, or ANT technologies) to connect one or more locations (e.g., schools, businesses, homes, consumer dwellings, network resources, etc.), servers 934, or to other devices, which may be similar or identical to the computer 902. Indeed, the system 900 may include more than one instance of each component (e.g., more than one computer 902, more than one display 936, and so forth).

Regardless of whether the computer 902 (or other device within the network 932) is portable or at a fixed location, it should be appreciated that, in addition to the input, output and storage peripheral devices specifically listed above, the computing device may be connected, such as either directly, or through the network 932 to a variety of other peripheral devices. In some example implementations, a single device may integrate one or more components shown in FIG. 9. For example, a single device may include the computer 902, image-capturing device 926, sensor 928, display 936 and additional components. In some example implementations, the sensor device 938 may comprise a mobile terminal having a display 936, image-capturing device 926, and one or more sensors 928. In other example implementations, the image-capturing device 926 or sensor 928 may be peripherals configured to be operatively connected to a media device, including for example, a portable gaming or media system.

Sensors, such as sensors 926 and 928, may be configured to detect or monitor at least one fitness parameter of a user 924. The sensors 926 and 928 may include, but are not limited to: an accelerometer, a gyroscope, a location-determining device (e.g., GPS), light (including non-visible light) sensor, temperature sensor (including ambient temperature or body temperature), sleep pattern sensors, heart rate monitor, image-capturing sensor, moisture sensor, force sensor, compass, angular rate sensor, or combinations thereof. The network 932 or the computer 902 may be in communication with one or more electronic devices of system 900, including for example, the display 936, an image capturing device 926 (e.g., one or more video cameras), and sensor 928, which may be an infrared (IR) device. In one example implementation, the sensor 928 may comprise an IR transceiver. For example, the sensors 926 and 928 may transmit waveforms into the environment, including towards the direction of the user 924 and receive a "reflection" or otherwise detect alterations of those released waveforms. In some example implementations, sensors may be passive, such as reflective materials that may be detected by image-capturing device 926 or sensor 928 (among others). In other example implementations, the image-capturing device 926 or sensor 928 may be configured to transmit or receive other wireless signals, such as radar, sonar, or audible information. It will be appreciated that signals corresponding to a multitude of different data spectrums may be utilized in accordance with various implementations. In this regard, the sensors 926 and 928 may detect waveforms emitted from external sources other than the system 900. For example, the sensors 926 and 928 may detect heat being emitted from the user 924 or the surrounding environment. Thus, the image-capturing device 926 and the sensor 928 may comprise one or more thermal imaging devices. In one example implementation, the image-capturing device 926 and the sensor 928 may comprise an IR device configured to perform range phenomenology. As an example, image-capturing devices configured to perform range phenomenology are commercially available from Flir Systems, Inc. of Portland, Oreg. Although the image capturing device 926, the sensor 928, and the display 936 are shown in direct (wirelessly or wired) communication with computer 902, it will be appreciated that these devices may directly communicate (wirelessly or wired) with the network 932.

Detected movements or parameters from any sensor(s) disclosed herein may include (or be used to form) a variety of different parameters, metrics or physiological characteristics including but not limited to speed, acceleration, distance, steps taken, calories, heart rate, sweat detection, effort, oxygen consumed, oxygen kinetics, angular rate, pressure, direction, rotational forces, impact forces, and combinations thereof. Such parameters may also be expressed in terms of activity points or currency earned by the user based on the activity of the user.

As seen in FIG. 9, the user 924 may possess, carry, or wear any number of devices, including sensory devices 938, 940, 942, or 944. One or more of the devices 938, 940, 942, or 944 may not be specially manufactured for fitness or athletic purposes. Indeed, aspects of this disclosure relate to utilizing data from a plurality of devices, some of which are not fitness devices, to collect, detect, or measure athletic data. In one example implementation, the device 938 may comprise a portable electronic device, such as a telephone or digital music player, including an IPOD®, IPAD®, or iPhone®, brand devices available from Apple, Inc. of Cupertino, Calif. or Zune® or Microsoft® Windows devices available from Microsoft of Redmond, Washington. It will be recognized that digital media players can serve as an output device, input device, or storage device for a computer. In some example implementations, the device 938 may be the computer 902, yet in other example implementations, the computer 902 may be entirely distinct from the device 938. Regardless of whether the device 938 is configured to provide certain output, it may serve as an input device for receiving sensory information. The devices 938, 940, 942, or 944 may include one or more sensors, including but not limited to any sensor known in the art or disclosed herein.

The devices 938-944 may communicate with each other, either directly or through a network, such as network 932.

Communication between one or more of the devices 938-944 may take place via the computer 902. For example, two or more of the devices 938-944 may be peripherals operatively connected to the bus 914 of the computer 902. In yet another example implementation, a first device, such as the device 938 may communicate with a first computer, such as the computer 902 as well as another device, such as the device 942, however, the device 942 may not be configured to connect to computer 902 but may communicate with the device 938. It will be appreciated that other configurations are possible. Also, the components shown in FIG. 10 may be included in the server 934, other computers, apparatuses, and so forth.

In some example implementations, the sensory devices 938, 940, 942 or 944 may be formed within or otherwise associated with the clothing of the user 924 or accessories of the user, including a watch, armband, wristband, necklace, shirt, shoe, or the like. Examples of wrist-worn devices (e.g., wrist-worn device 800) were described above, however, these are merely example implementations and this disclosure should not be limited to such. These devices may be configured to monitor athletic movements of a user, including all-day activity of the user 924. The devices may detect athletic movement when the user 924 interacts with the computer 902 or operate independently of the computer 902. For example, each device may be configured to function as an-all day activity monitor that measures activity regardless of the proximity of the user 924 to or interactions with the computer 902.

In some example implementations, sensors, such as the sensors 944 shown in FIG. 9, may be integrated into apparel, such as athletic clothing. For instance, the user 924 may wear one or more on-body sensors 944a-b. The sensors 944 may be incorporated into the clothing of the user 924 or placed at any desired location of the body of user 924. The sensors 944 may communicate (e.g., wirelessly) with the computer 902; the sensors 928, 938, 940, and 842; or the camera 926. Examples of interactive gaming apparel are described in U.S. patent application Ser. No. 10/286,396, filed Oct. 30, 2002, and published as U.S. Pat. Pub, No. 2004/0087366, which is incorporated by reference herein in its entirety. In some example implementations, passive sensing surfaces may reflect waveforms, such as infrared light, emitted by the image-capturing device 926 or the sensor 928. In one example implementation, passive sensors located on apparel of the user 924 may comprise generally spherical structures made of glass or other transparent or translucent surfaces which may reflect waveforms. Different classes of apparel may be utilized in which a given class of apparel has specific sensors configured to be located proximate to a specific portion of the body of the user 924 when properly worn. For example, golf apparel may include one or more sensors positioned on the apparel in a first configuration and yet soccer apparel may include one or more sensors positioned on apparel in a second configuration.

Figure 11:
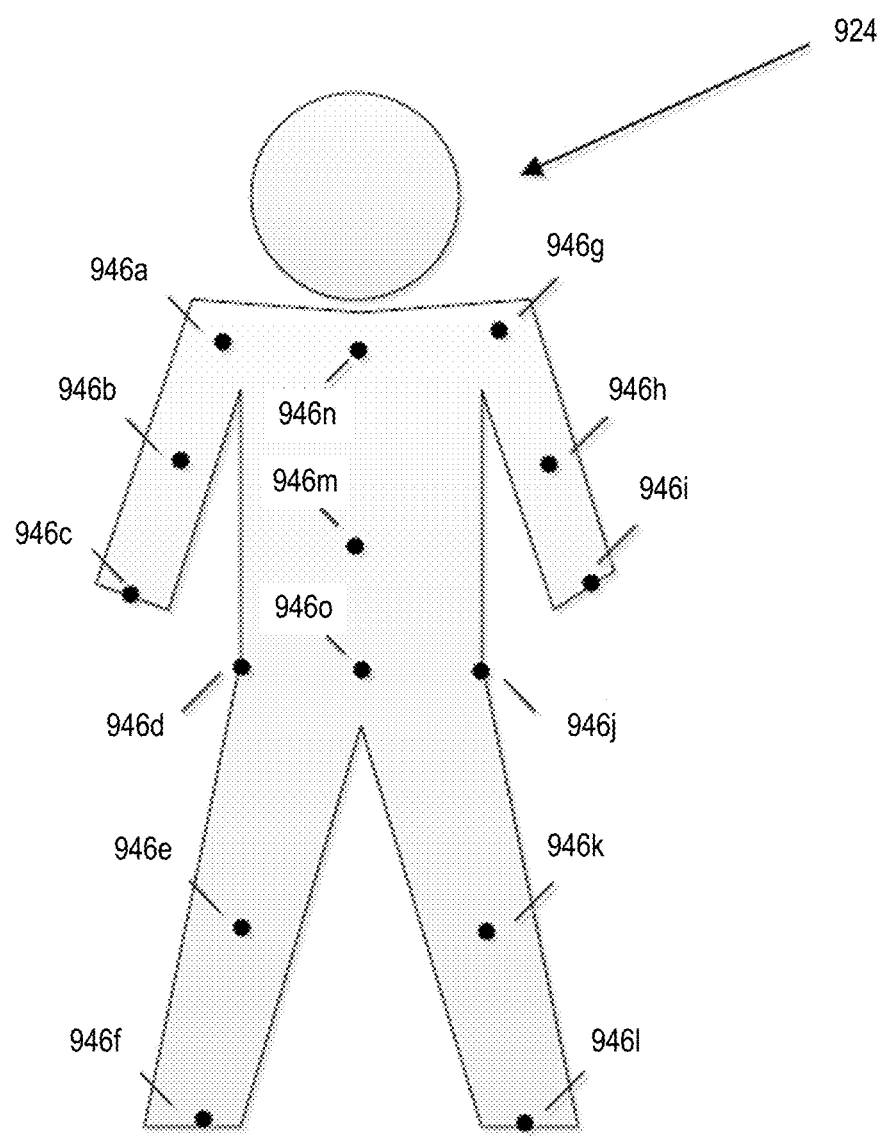
FIG. 11 is an illustration of example locations on the body of the user where sensors may be located to measure the movements of the user.

FIG. 11 shows illustrative locations for sensory input (e.g., sensory locations 946a-946o). In this regard, sensors may be physical sensors located on or in the clothing of a user in some example implementations. In example implementations, the sensor locations 946a-946o may be based upon identification of relationships between two moving body parts. For example, sensor location 946a may be determined by identifying motions of the user 924 with an image-capturing device, such as image-capturing device 926. Thus, in some example implementations, a sensor may not physically be located at a specific location (such as sensor locations 946a-946o), but is configured to sense properties of that location, such as with image-capturing device 926 or other sensor data gathered from other locations. In this regard, the overall shape or portion of the body of the user 924 may permit identification of certain body parts. Regardless of whether an image-capturing device, such as camera 926, is utilized or a physical sensor located on the user 924, or using data from other devices, the sensors may sense a current location of a body part or track movement of the body part. In one example implementation, sensory data relating to location 946m may be utilized in a determination of the center of gravity (i.e., center of mass) of the user 924. For example, relationships between the sensor location 946a and the sensor locations 946f or 946l with respect to one or more of the sensor locations 946m-946o may be utilized to determine if the center of gravity has been elevated along the vertical axis (such as during a jump) or if a user is attempting to "fake" a jump by bending and flexing their knees. In one example implementation, the sensor location 946n may be located at about the sternum of the user 924. Likewise, the sensor location 946o may be located approximate to the naval of user 924. In some example implementations, data from the sensor locations 946m-946o may be utilized (alone or in combination with other data) to determine the center of gravity for the user 924. In some example implementations, relationships between multiple several sensor locations, such as sensor locations 946m-946o, may be utilized in determining orientation of the user 924 or rotational forces, such as twisting of the torso of the user 924. Further, one or more sensor locations may be utilized to determine a center of moment location. For example, one or more of the sensor locations 946m-946o may serve as a point for a center of moment location of the user 924. In another example implementations, one or more of the sensor locations may serve as a center of moment of specific body parts or regions.

Further aspects of this disclosure relate to determinations of when a user, such as the user 924, is active or inactive. Some example implementations may relate to altering electronic outputs, such as rewards (e.g., rewarding or deducting virtual or physical awards), based upon activity levels. In this regard, determinations of activity or inactivity may be utilized as an adjustment criterion. For example, energy expenditure values may be determined and energy expenditure points may be deducted when the user 924 has been inactive for a predetermined period of time or enhanced when certain criteria are met. This feature may be included with all calculations or may be used in various games and competitions. For example, it may be determined whether an adjustment criterion has been met. The adjustment criterion may include inactivity for a predetermined time period. In some example implementations inactivity is not determined by merely determining that an amount of time has passed since with user was active.

When an adjustment criterion has been met, a reward, such as for example, energy expenditure points, may be adjusted. The adjustment may be a function of a property of the detected inactivity (e.g., duration, intensity, type, threshold, specific biometric or physiological parameter, etc.). In some example implementations, a device or alarm may inform the user 924 (or authorized groups/individuals) that the user: (a) may be close to receiving a reduction in an award, such as energy expenditure points, to encourage activity; or (b) that user received a reduction of energy expenditure points. Thus, teammates or competing users may be notified of a reduction (or potential for reduction), and teachers, trainers, or parents may more readily monitor the physical activity of others. In some example implementations, a device, such as device 800 (FIG. 8), or any other device disclosed herein, may be configured to sense activity levels and detect that the user has been in a non-active (e.g., low activity) state for a predetermined amount of time, and in response, transmit an alert message to a local or remote output device to remind the user to become more active.

The property of the detected inactivity (duration, intensity, etc.) may be conducted at various intervals and allow for tracking points concurrently for different time periods, such as days, weeks and years. The threshold levels of a low activity state and amount of inactive time could also vary and be individually set by the user 924 or any other individual or group.

In some arrangements, user non-activity or inactivity may also be detected and affect progress toward completion of an activity goal. For example, inactivity may be detected when a user does not exhibit movement of a particular level or a type of movement for a specified amount of time, does not exhibit a heart rate of at least a threshold level, does not move a sufficient amount of distance over an amount of time and the like or combinations thereof. For arrangements in which a user accumulates activity points to reach an activity point goal, points or a value may be deducted from the activity points or other activity metric total when an amount of non-activity (e.g., inactivity or sedentary state) is detected. Various conversion rates for converting inactivity to activity point deductions may be used. In one example, 10 minutes of inactivity may correspond to a 5 point deduction. In another example, 30 minutes of inactivity may correspond to a 100 point deduction. Loss or deduction of activity points may be linear or may be non-linear, for example, exponential, parabolic and the like.

Non-active time may include inactive time and sedentary time. Inactivity and sedentary time may be defined by different movement, heart-rate (or other physiological parameter), step or other thresholds or may be defined using the same thresholds. In one example, sedentary time may have a higher threshold (e.g., requiring a higher level of activity) than an inactivity threshold. That is, an individual may be considered sedentary but not inactive. The non-active threshold may correspond to the sedentary threshold or a higher threshold, if desired. Alternatively, an inactivity threshold may be greater than a sedentary threshold. There may also be multiple sedentary thresholds, inactivity thresholds or non-active thresholds (e.g., each of the sedentary and inactivity thresholds may be a non-active threshold). Different point deductions or rates of point deductions may also be defined between the multiple thresholds and levels of little to no activity (e.g., non-activity). For example, a user may lose 50 points per hour for inactivity and 30 points per hour for sedentary activity or vice versa. Further, activity point deduction may be triggered at different times depending on if the user is inactive or sedentary. For instance, a user may begin losing activity points after 30 minutes of inactivity or 45 minutes of being sedentary. Additional thresholds (e.g., more than two thresholds) and corresponding rates of activity point loss may also be defined.

In some arrangements, various sensors may be used to detect non-active periods of time. As discussed, non-activity time periods may be defined based on heart-rate, amplitude of a movement signal, step rate (e.g., <10 steps per minute), or the like. Alternatively or additionally, inactivity and sedentary time periods may be measured based on a physical position, body position, body orientation, body posture of or type of activity being performed by the individual. The detrimental effects of various physical inactivity or sedentary body positions or orientations may also differ. Accordingly, 30 minutes of reclining may introduce the same health risks as 45 minutes of sitting. The potential for health risks may also be time-dependent. Accordingly, non-activity (e.g., sleeping) for a specified range of durations and during a specified range of time might not introduce health risks. In one example, sleeping for 7-9 hours between 9 PM and 9 AM might not introduce detrimental health risks and thus, might not contribute to activity point or other activity metric value deduction. Indeed, in some example, a lack of inactivity (such as sleep) for a specified range of durations or during a specified range of time may be considered detrimental to the health of a user. Thus, activity points may be deducted or activity points may be accumulated at a slower rate during these times.

Additionally or alternatively, the amount by which a value of the activity metric (e.g., an activity points) is decreased may be determined based on time of day, location of the user, physical position of the user, level of inactivity and the like. For example, a user may lose greater value in an activity metric or at a faster rate during the afternoon than during the evenings. In another example, if a user is at a gym, the user may lose fewer activity points or other activity metric or lose value in the metric at a slower rate than if the user was located at home.

To account for the variances in types of non-active activity (e.g., below a requisite level of movement to be considered activity), a system may distinguish between physical body positions or orientations including, for example, sleeping, reclining, sitting and standing. Distinguishing between different physical body positions and orientations may be determined from sensors at different locations of the body of the user (or sensors configured to detect locations of certain body parts). The physical body position of the user may then be determined based on the relative positions of the body parts to one another. For example, when a knee location sensor is within a first threshold distance of a waist or chest sensor, the system may determine that the user is sitting. If the knee location sensor is outside of the first threshold distance, the system may determine that the user is standing. In other examples, an angle formed by the various sensors may be used to determine an individual's position. Additionally or alternatively, the location of the various body parts of a user may be evaluated in conjunction with accelerometer or movement data to determine if the user is exhibiting movement or (e.g., at, above or below) a specified level of movement.

In addition to deductions in activity points, the system may alert a user to inactivity to encourage active lifestyles. In one example, the system may alert the user (or authorized individuals or groups) by displaying a message or indicator on a device, such as any device described herein, after a specified amount of inactivity such as 2 minutes, 5 minutes, 30 minutes, 1 hour and the like. The amount of inactivity time may be additive over non-consecutive time periods. An amount of consecutive inactivity time may alternatively or additionally be tracked. For example, if the user is inactive between 10:15 and 11:00 AM and then again between 2:00 and 2:30 PM, the total amount of non-active time may be 1 hour and 15 minutes. The message or indicator of inactivity may be provided as a warning prior to deducting activity points. For example, the message may indicate that X amount of activity points will be deducted if the user does not exhibit a sufficient level of activity within a specified amount of time (e.g., 30 minutes, 5 minutes, 10 seconds, 30 seconds, 1 hour, 2 hours, etc.). Accordingly, the device may include a non-active timer to determine the amount of user non-activity. Additionally, the message may provide a suggestion as to a type of activity the user should perform to counter any risks introduced by the inactivity. For example, the system may suggest that the user walk 1 hour at a 10 minute mile pace. When the user has counteracted or accounted for the risks or negative effects of the detected amount of inactivity time, a celebratory message or other indication may be provided.

Warnings, point deductions, or other notifications may be provided if a user returns to a sedentary or a non-active mode within a specified amount of time of exiting sedentary or a non-active mode. For example, the user may exercise or exhibit a sufficient level of activity to exit the sedentary or a non-active mode for a period of 10 minutes. However, the system or device may require at least 30 minutes of activity to avoid additional warnings for a period of time such as 1 hour, 2 hours, 3 hours, etc. For example, the warnings may indicate that the user did not exhibit activity for a sufficient amount of time or a sufficient level of activity or a combination thereof. Additionally, multiple sedentary periods within short amounts of time (e.g., a threshold amount of time) may require higher or additional levels of activity to counteract potential sedentary effects including health risks and the like. In a particular example, the user may be required to perform a higher level of activity to halt point deduction.

The device or other system may further advise a user as to an amount of non-active time allowed before negative health effects may occur. In one example, the device or system may include a countdown indicating a remaining amount of allowable non-active time before potential health risks may begin taking effect. An amount of permissible non-active time may be earned or accumulated based on an amount of activity performed. Accordingly, the device may also provide suggestions or recommendations as to a type or duration of activity that may be performed to earn a specified amount of non-active time (e.g., 1 hour of TV watching). Different types of non-active or sedentary activities may require different types or amounts of activity. For example, 1 hour of reclining may require more strenuous or longer exercise than 1 hour of sitting. In another example, 1 hour of sitting while knitting may require less strenuous or a lower amount of exercise or activity than 1 hour of sitting while watching television. According to one or more arrangements, recommendations may be generated based on empirical data or predefined programming and data tables specifying a type or duration of activity and a corresponding amount of permissible non-activity.

The device or activity tracking system may further recommend activities based on historical records. For instance, the device or tracking system may determine activity performed by the user in the past and generate recommendations based on those types of activities. Additionally or alternatively, the device or tracking system may generate recommendations for specific workouts performed by the user in the past. For example, a user may need to perform 500 calories worth of activity to counteract 2 hours of TV watching. In such a case, the system may recommend a particular workout performed by the user in the past in which the user burned 500 calories. Combinations of historical activity types and specific historical workouts may be used to generate recommendations. In one example, the system may recommend one of two workouts that the user has performed in the past based on a type of workout that the user appears to prefer. The preference may be determined based on a number of times the user has performed each type of workout. A workout or activity type may also be recommended based on location and time. For example, if a user previously performs a particular type of activity or a particular workout routine at the same location or at the same time, the system may recommend that type of activity or workout routine. Other recommendations algorithms and factors may be used.

The system 900 (FIG. 9) may be configured to transmit energy expenditure points to a social networking website. The users may be ranked based on their total number of points for a desired time interval (e.g., rank by day, week, month, year, etc.).

Aspects of the disclosure have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the disclosure.

What is claimed is:

1. A method of determining heart rate, the method comprising:
   (a) illuminating skin of a user with an illumination source, the illumination source comprising a near-field illumination source and a far-field illumination source wherein the near-field illumination source comprises a first lens element configured to focus first electromagnetic radiation provided by the near-field illumination source such that the first electromagnetic radiation achieves maximum reflection with the skin positioned a first distance from an illumination detector and wherein the far-field illumination source comprises a second lens element configured to focus second electromagnetic radiation provided by the far-field illumination source such that the second electromagnetic radiation achieves maximum reflection with the skin positioned a second distance, greater than the first distance, from the illumination detector;
   (b) detecting electromagnetic radiation reflected off the skin of the user with the illumination detector, the electromagnetic radiation detected comprising a first amount, N, of electromagnetic radiation provided by the near-field illumination source and a second amount, F, of electromagnetic radiation provided by the far-field illumination source;
   (c) determining a position of the skin of the user relative to the illumination detector based on the electromagnetic radiation reflected wherein determining the position comprises calculating a ratio of the first amount of electromagnetic radiation reflected and the second amount of electromagnetic radiation reflected; and
   (d) determining, at a processor, a heart rate of the user wherein determining the heart rate comprises analyzing information corresponding to the electromagnetic radiation reflected and compensating for the position of the skin of the user.

2. The method of claim 1, wherein the illumination source comprises at least one light-emitting diode (LED).

3. The method of claim 2 wherein the at least one LED is configured to generate infrared (IR) illumination.

4. The method of claim 1 wherein the illumination detector comprises a photodiode.

5. The method of claim 1 wherein the ratio is equal to N/F.

6. The method of claim 1 wherein:
   step (c) comprises accessing a lookup table that associates skin positions with respective compensation factors; and
   step (d) includes receiving a compensation factor associated with the position of the skin of the user and utilizing the compensation factor when determining the heart rate of the user.

7. A heart rate determination system comprising:
   a processor;
   an illumination source configured to illuminate skin of a user, the illumination source comprising a near-field illumination source and a far-field illumination source;
   an illumination detector that detects electromagnetic radiation reflected off the skin of the user, the electromagnetic radiation detected comprising a first amount, N, of electromagnetic radiation provided by the near-field illumination source and a second amount, F, of electromagnetic radiation provided by the far-field illumination source;
   a first lens element configured to focus first electromagnetic radiation provided by the near-field illumination source such that the first electromagnetic radiation achieves maximum reflection with the skin positioned a first distance from the illumination detector;
   a second lens element configured to focus second electromagnetic radiation provided by the far-field illumination source such that the second electromagnetic radiation achieves maximum reflection with the skin positioned a second distance, greater than the first distance, from the illumination detector; and
   memory storing instructions that, when executed by the processor, cause the processor to:
      determine a position of the skin of the user relative to the illumination detector, and
      determine a heart rate of the user by analyzing information corresponding to an amount of the electromagnetic radiation detected by the illumination detector and compensating for the position of the skin of the user.

8. The heart rate determination system of claim 7 wherein the near-field illumination source comprises a near-field light-emitting diode (LED) and the far-field illumination source comprises a far-field light-emitting diode.

9. The heart rate determination system of claim 8 wherein:
   the instructions, when executed by the processor, further cause the processor to determine a compensation factor based on a ratio of the first amount of electromagnetic radiation, N, to the second amount of electromagnetic radiation, F.

10. The heart rate determination system of claim 9 further comprising:
    a lookup table that associates skin positions with respective compensation factors; and
    the instructions, when executed by the processor, further cause the processor to perform a lookup at the lookup table using the ratio and provide a compensation factor associated with the ratio to the processor.

11. The heart rate determination system of claim 8 wherein the illumination source is a first illumination source, the near-field LED is a first near-field LED, and the far-field LED is a first far-field LED and further comprising:
    a second illumination source that comprises a second near-field LED and a second far-field LED.

12. The heart rate determination system of claim 11 wherein the first illumination source and the second illumination source are positioned substantially orthogonal to each other.

13. The heart rate determination system of claim 11 wherein:
   the first near-field LED is positioned between the illumination detector and the first far-field LED; and
   the second near-field LED is positioned between the illumination detector and the second far-field LED.

14. The heart rate determination system of claim 7 wherein the illumination detector comprises a photodiode.

15. The heart rate determination system of claim 7 wherein the heart rate determination system is incorporated into a wrist-worn device that is configured to measure movements of an individual wearing the wrist-worn device.

\* \* \* \* \*